(12) United States Patent
Donhowe

(10) Patent No.: US 9,055,865 B2
(45) Date of Patent: Jun. 16, 2015

(54) METHOD AND SYSTEM FOR MEASURING INSERTED LENGTH OF A MEDICAL DEVICE USING INTERNAL REFERENCED SENSORS

(75) Inventor: Caitlin Donhowe, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1088 days.

(21) Appl. No.: 12/613,698

(22) Filed: Nov. 6, 2009

(65) Prior Publication Data

US 2010/0121145 A1 May 13, 2010

Related U.S. Application Data

(60) Provisional application No. 61/113,444, filed on Nov. 11, 2008.

(51) Int. Cl.
| | |
|---|---|
| A61B 1/04 | (2006.01) |
| A61B 1/00 | (2006.01) |
| A61B 1/005 | (2006.01) |
| A61B 5/06 | (2006.01) |

(52) U.S. Cl.
CPC .............. *A61B 1/0051* (2013.01); *A61B 5/065* (2013.01)

(58) Field of Classification Search
None
See application file for complete search history.

(56) References Cited

U.S. PATENT DOCUMENTS

| | | | |
|---|---|---|---|
| 6,468,203 B2 | 10/2002 | Belson | |
| 6,610,007 B2 * | 8/2003 | Belson et al. | 600/146 |
| 2003/0191367 A1 * | 10/2003 | Belson et al. | 600/146 |
| 2004/0176683 A1 | 9/2004 | Whitin et al. | |
| 2004/0249269 A1 * | 12/2004 | Shiono et al. | 600/424 |
| 2006/0258912 A1 * | 11/2006 | Belson et al. | 600/152 |
| 2007/0135803 A1 | 6/2007 | Belson | |
| 2007/0249901 A1 * | 10/2007 | Ohline et al. | 600/117 |
| 2007/0270650 A1 | 11/2007 | Eno et al. | |
| 2008/0234700 A1 | 9/2008 | Trovato et al. | |
| 2008/0287963 A1 | 11/2008 | Rogers et al. | |
| 2009/0099420 A1 | 4/2009 | Woodley et al. | |
| 2009/0137952 A1 * | 5/2009 | Ramamurthy et al. | 604/95.01 |
| 2009/0216083 A1 | 8/2009 | Durant et al. | |
| 2010/0121148 A1 | 5/2010 | Donhowe et al. | |
| 2010/0121151 A1 | 5/2010 | Donhowe et al. | |

OTHER PUBLICATIONS

Vertut, Jean and Philippe Coiffet, *Teleoperation and Robotics: Evolution and Development*, 1986, 332 pages, English translation: Prentice-Hall, Inc., Inglewood Cliffs, NJ, USA.

* cited by examiner

*Primary Examiner* — Anhtuan T Nguyen
*Assistant Examiner* — Alexandra Newton

(57) ABSTRACT

Measured locations of position sensors on a steerable medical device are used to determine the insertion depth of the steerable medical device with respect to a foundation point, which is initialized by an operator. The insertion depth, in turn, is used to determine the state of each segment that has passed the foundation point, i.e., is distal to the foundation point.

20 Claims, 12 Drawing Sheets

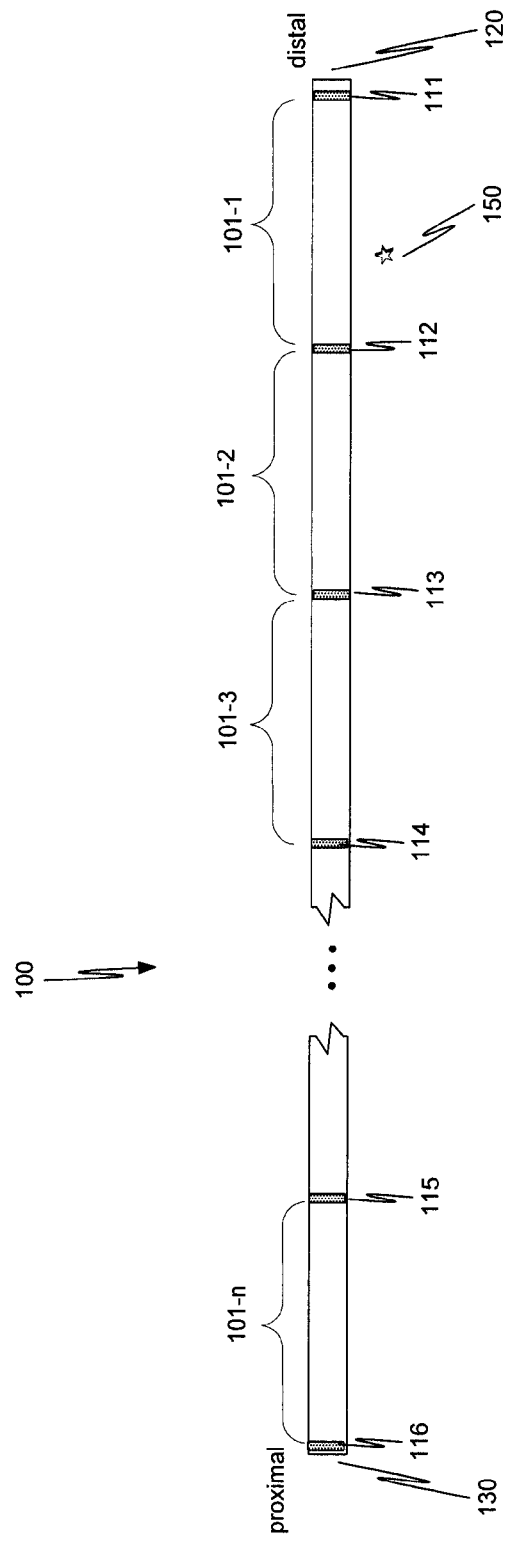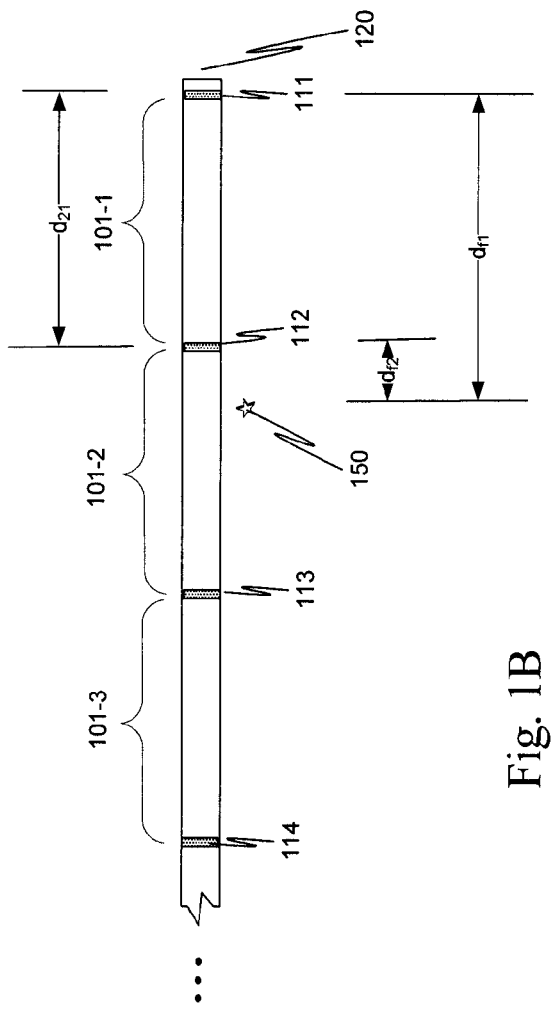
Fig. 1A
Fig. 1B

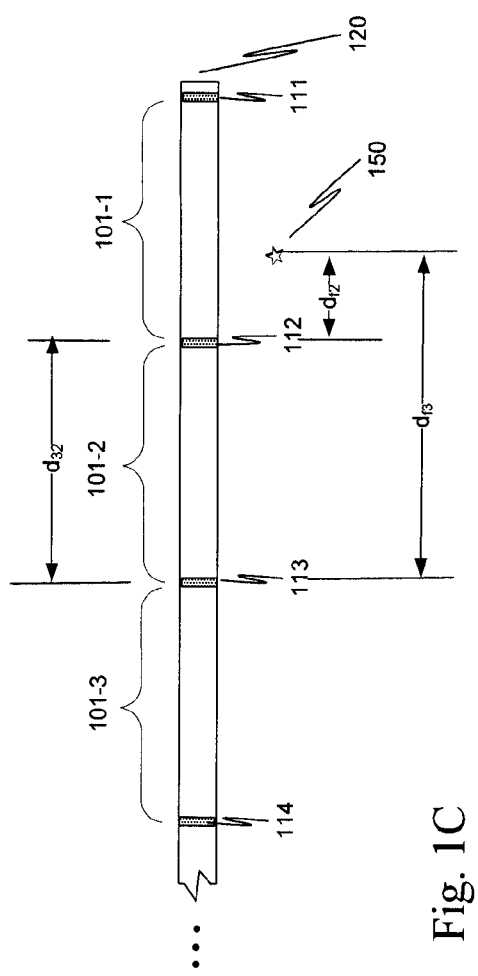
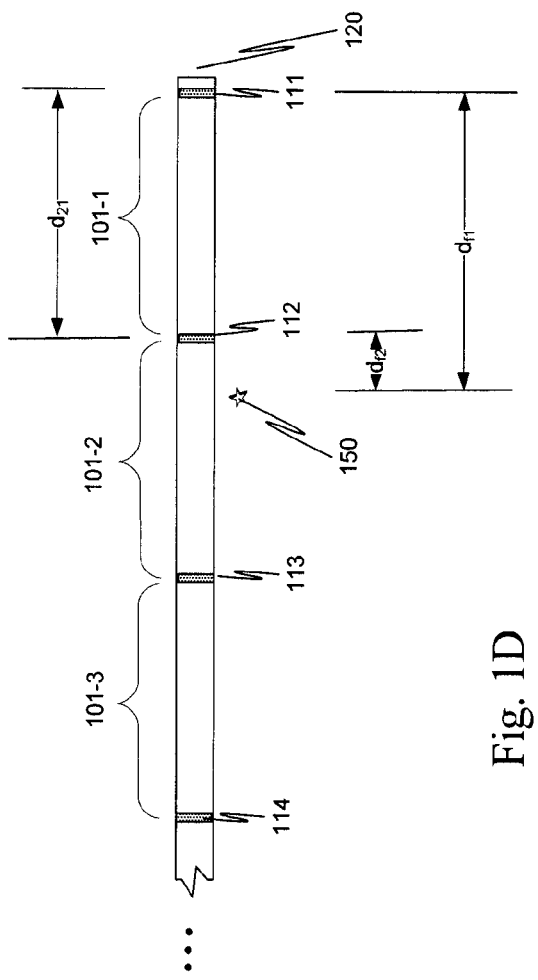
Fig. 1C
Fig. 1D

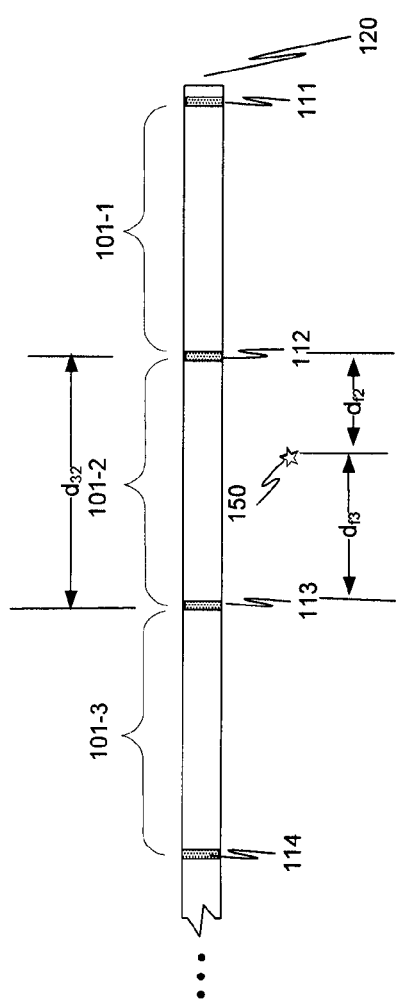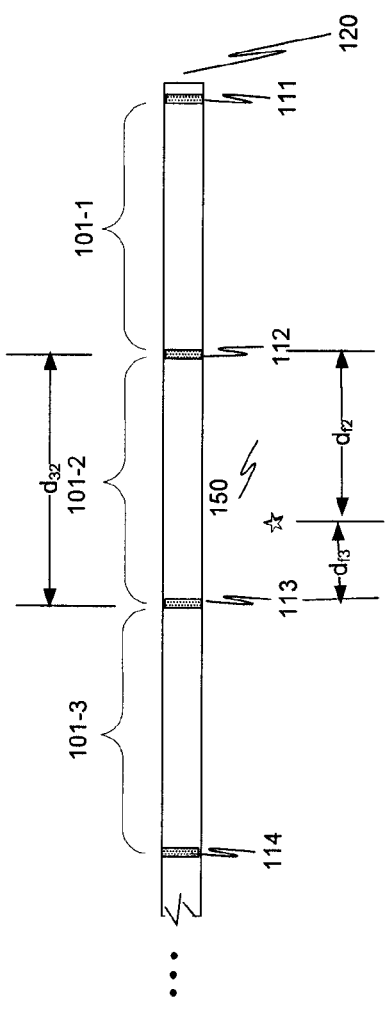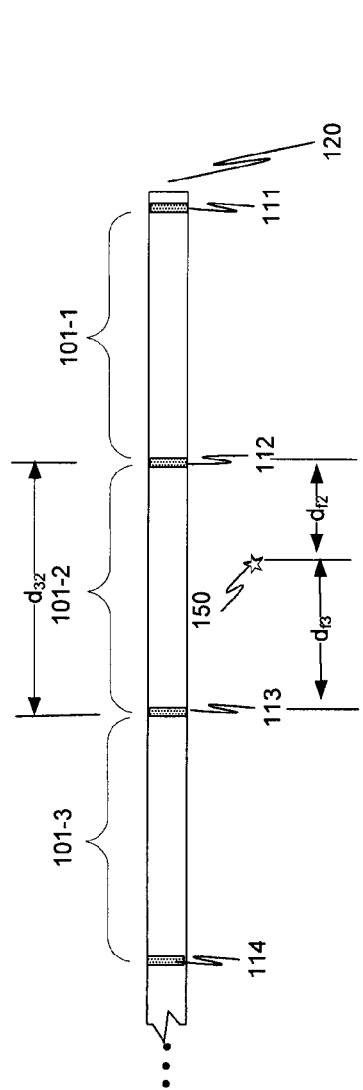

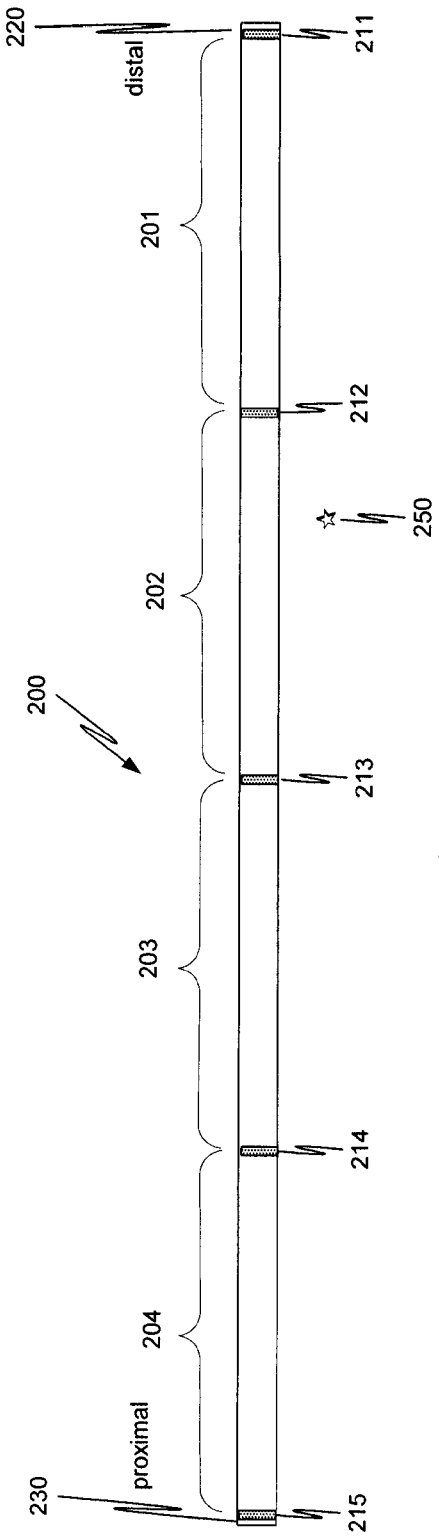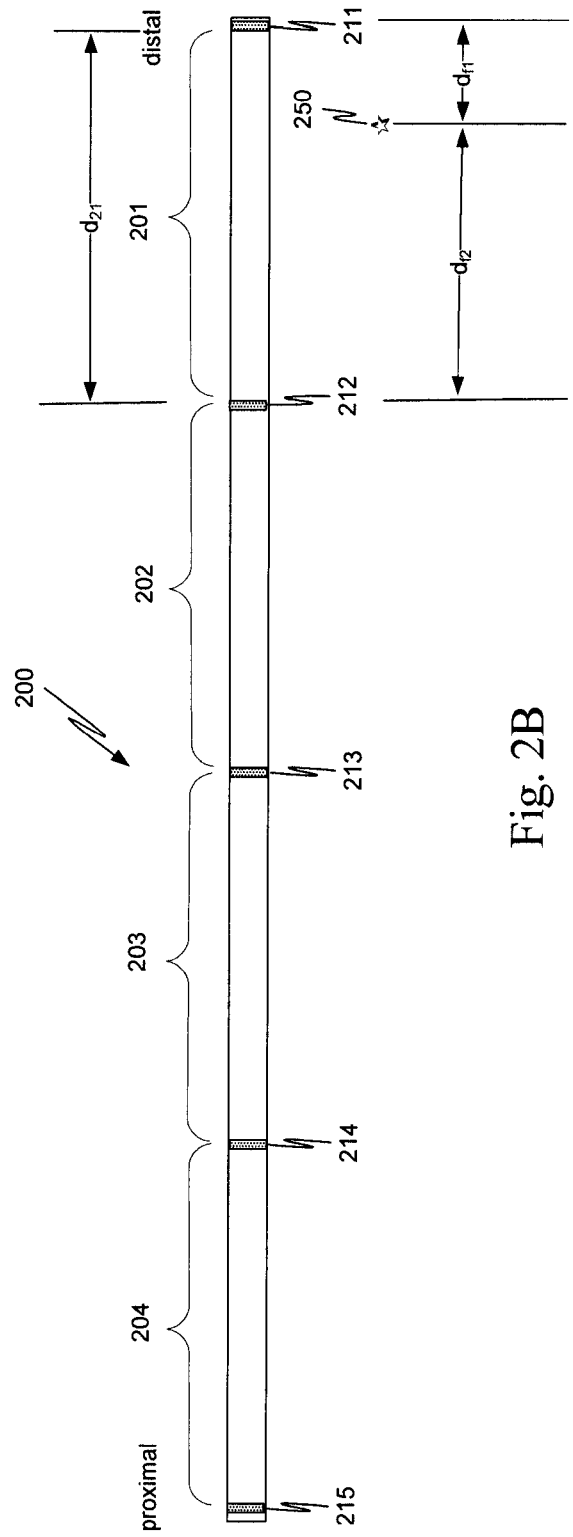
Fig. 2A
Fig. 2B

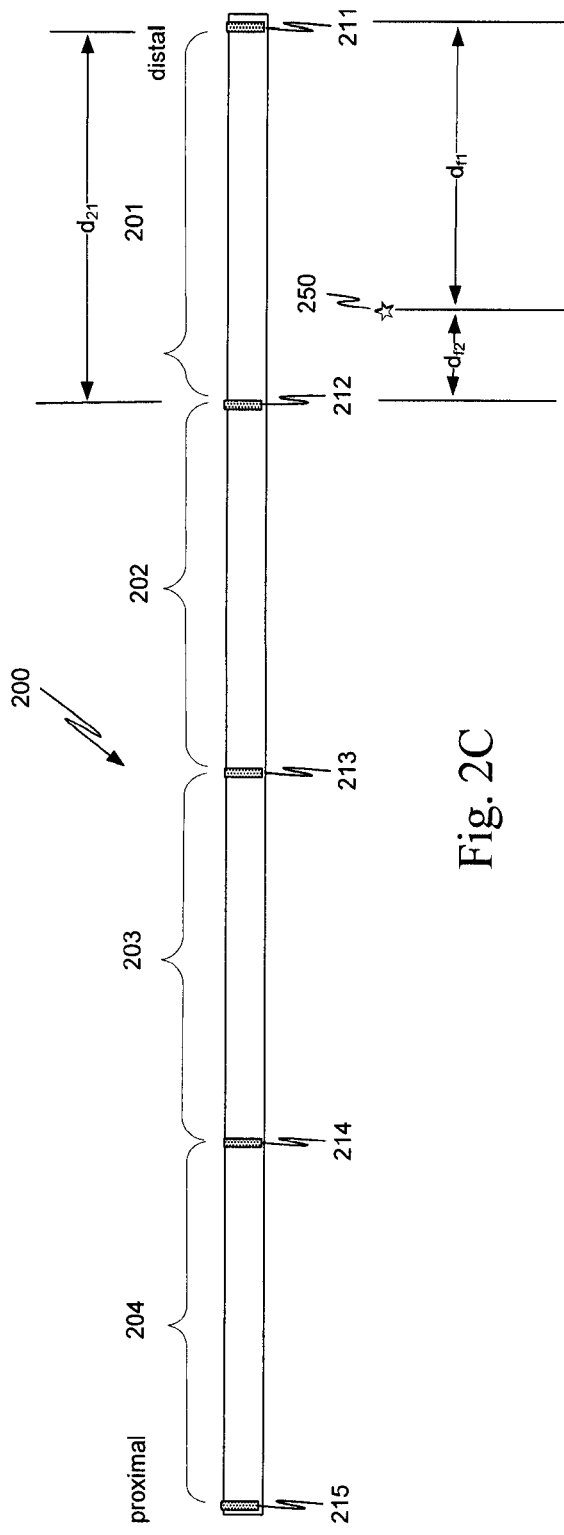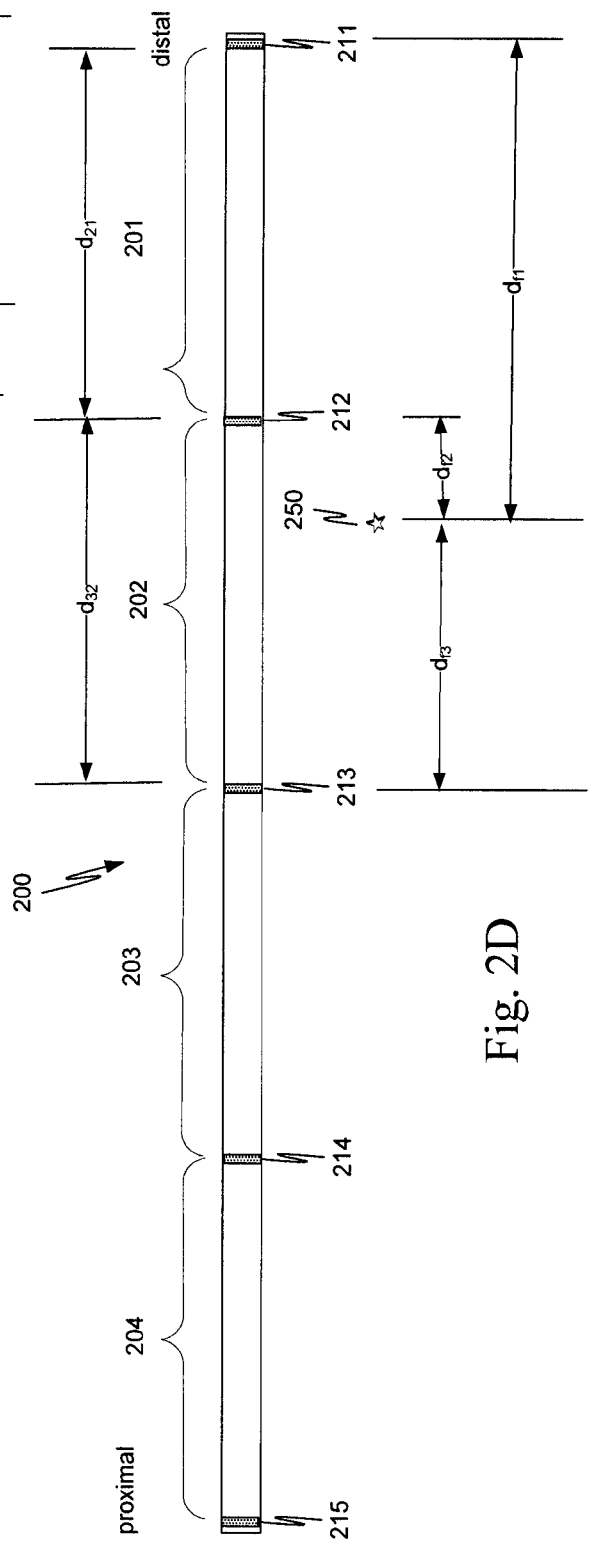
Fig. 2C
Fig. 2D

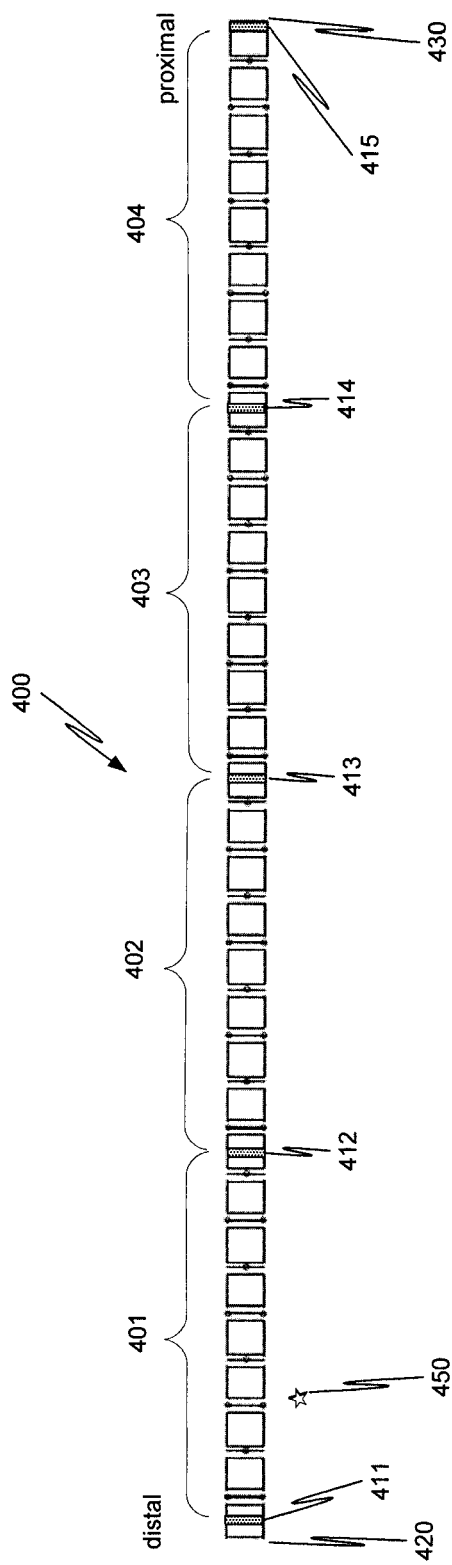
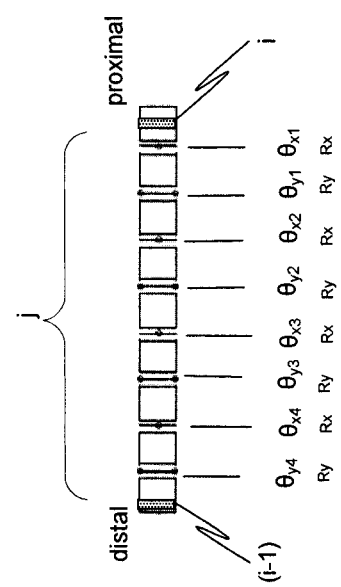
Fig. 4A
Fig. 4B

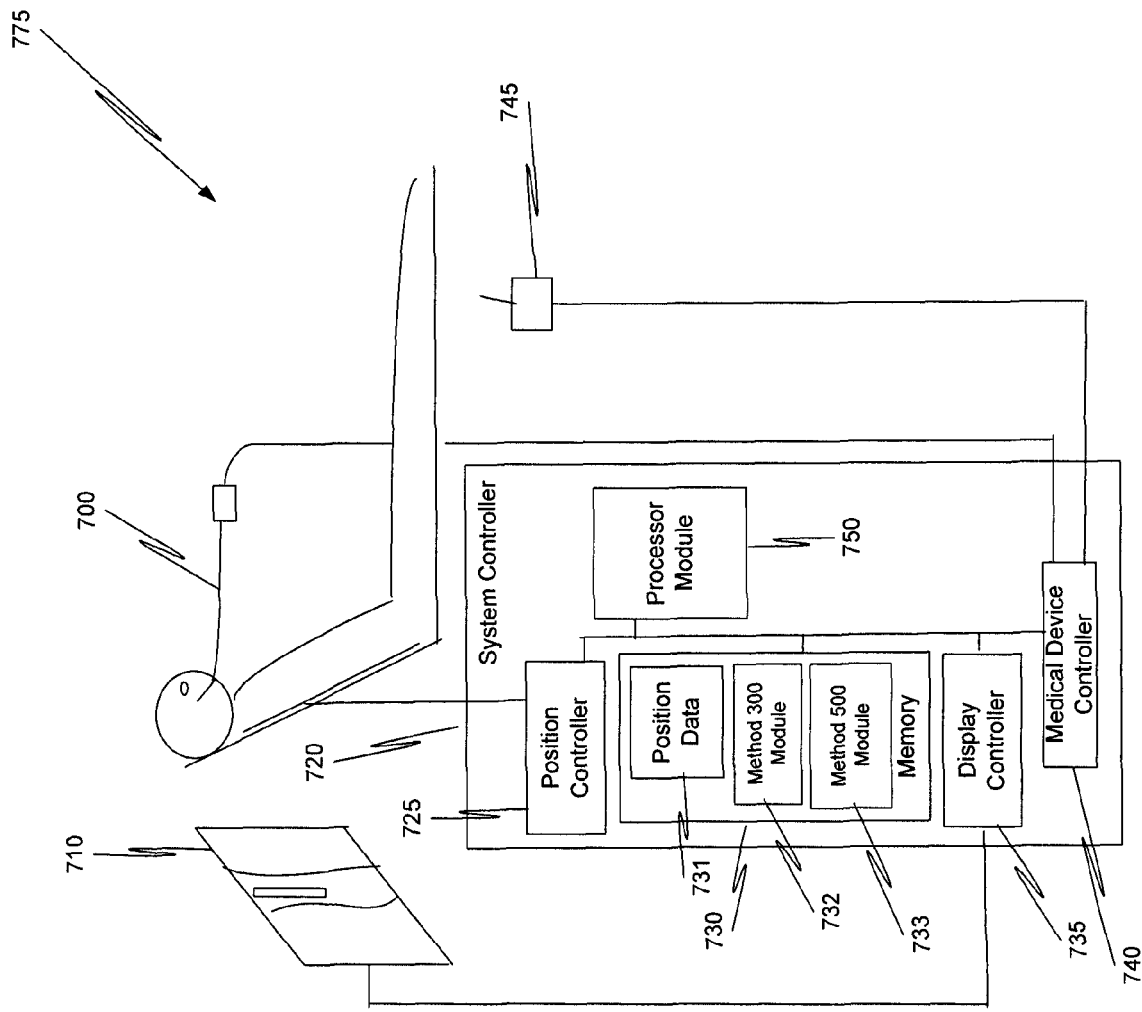

METHOD AND SYSTEM FOR MEASURING INSERTED LENGTH OF A MEDICAL DEVICE USING INTERNAL REFERENCED SENSORS

RELATED APPLICATION

The present application claims the benefit of U.S. Provisional Patent Application No. 61/113,444 filed Nov. 11, 2008 entitled "Methods for Measuring the Inserted Length of an Endoscope Based Using Internal Global-Referenced Sensors" naming as inventor, Caitlin Donhowe, the entirety of which is hereby incorporated by reference.

BACKGROUND

1. Field of Invention

Aspects of this invention are related to measuring the inserted length of an endoscope, and more particularly to measuring the inserted length of an endoscope without an external position sensor at the body entry point of the endoscope.

2. Related Art

An endoscope is a medical instrument for visualizing the interior of a patient's body. Endoscopes have been used for a variety of medical diagnostic procedures and for a variety of medical interventional procedures.

Many different types of endoscopes are known. For example, one steerable endoscope has an elongated body with a steerable distal portion and an automatically controlled proximal portion. Such an endoscope is described in U.S. Pat. No. 6,468,203 B2, entitled "Steerable Endoscope and Improved Method of Insertion," of Amir Belson issued on Oct. 22, 2002, which is incorporated herein by reference in its entirety.

A common problem with using an endoscope is determining the insertion depth of the endoscope during the procedure. One way to determine the insertion depth is to use an external position sensor at the entry point of the endoscope into the body of the patient. See for example, U.S. Patent Application Publication No. US 2007/0249901 A1 published on Oct. 25, 2007 for U.S. patent application Ser. No. 11/648,408, entitled "Instrument Having Radio Frequency Identification Systems and Method for Use," of Ohline et al. filed on Dec. 28, 2006.

SUMMARY

Unlike prior art methods that required an external position sensor to determine the insertion depth of a steerable medical device, the measured locations of position sensors on a steerable medical device are used to determine the insertion depth of the steerable medical device with respect to a foundation point. The foundation point, in one aspect, is initialized by an operator. The insertion depth, in turn, is used to determine the state of each medical device segment that has passed the foundation point, i.e., each segment that is distal to the foundation point.

In one aspect, a set of position data from a plurality of position sensors on the steerable medical device is received by a processor. The steerable medical device includes a plurality of segments. In one embodiment, a segment is bounded by a pair of the position sensors such that the number of position sensors is one more than the number of segments.

The processor generates a number of active segments of the steerable medical device and a number of articulating segments of the steerable medical device using the set of position data and a location of a foundation point. The processor sends a command to the controller for the steerable medical device to configure the steerable medical device to have the number of active segments and the number of articulating segments.

To generate the number of active segments of the steerable medical device and the number of articulating segments, the processor analyzes data of a first position sensor located on the proximal end of the most proximal currently active segment to determine a position of the first position sensor relative to the foundation point. The processor also analyzes data of a second position sensor located on the distal end of the most proximal currently active segment to determine a position of the second position sensor relative to the foundation point.

The analyzing includes generating a distance $d_{fi}$ from the proximal position sensor to the foundation point. The analyzing also includes generating a distance $d_{f(i-1)}$ from the distal position sensor to the foundation point, and generating a distance $d_{i(i-1)}$ from the proximal position sensor to the distal position sensor.

After determination of the distances, in one aspect, the processor compares the distance $d_{fi}$ and the distance $d_{f(i-1)}$ to determine whether distance $d_{fi}$ is less than distance $d_{f(i-1)}$. The processor changes the number of articulating segments upon finding that the distance $d_{fi}$ is less than distance $d_{f(i-1)}$ if the most proximal active segment does not already have state articulating.

In another aspect, the processor compares the distance $d_{fi}$ and the distance $d_{i(i-1)}$ to determine whether distance $d_{fi}$ is greater than distance $d_{i(i-1)}$. The processor changes the number of active segments upon finding distance $d_{fi}$ is greater than distance $d_{i(i-1)}$.

In another aspect, each segment includes a plurality of links. In this aspect, generating the number of active segments of the steerable medical device and the number of articulating segments of the steerable medical device includes generating locations of a plurality links in a segment using a kinematic model for the segment. A centerline representation of the steerable medical device is generated using the locations. An insertion depth of the steerable medical device is generated using the centerline representation.

In one aspect, the processor is included in an apparatus that also includes a memory coupled to the processor. The memory has instructions stored therein. Executing the instructions on the processor performs the various operations described above.

In yet another aspect, an apparatus includes a steerable medical device. The steerable medical device includes a plurality of articulatable segments and a plurality of position sensors.

This apparatus also includes a controller coupled to the steerable medical device. The controller includes (i) a processor coupled to the steerable medical device to receive position data from the plurality of sensors and to receive data defining a foundation point, and (ii) a steerable medical device controller coupled to the steerable medical device to configure the plurality of articulatable segments.

The processor analyzes the position data with reference to the foundation point to generate a number of the plurality of segments having an active state and a number of the plurality of segments having an articulating state. The processor outputs a command to the steerable medical device controller to configure the steerable medical device to have the number of the plurality of segments having the active state and the number of the plurality of segments having the articulating state.

BRIEF DESCRIPTION OF THE DRAWINGS

FIG. 1A is a diagrammatic view of a steerable endoscope.

FIGS. 1B to 1G illustrate movement of the steerable endoscope relative to a foundation point.

FIG. 2A is a diagrammatic view of another steerable endoscope.

FIGS. 2B to 2E illustrate movement of the steerable endoscope relative to a foundation point.

FIG. 4A is a diagrammatic view of yet another steerable endoscope.

FIG. 4B is a diagrammatic view of elements of a kinematic model used to analyze locations of links in the steerable endoscope of FIG. 4A.

FIG. 7 is a diagrammatic view of an apparatus used in one aspect of the processes and operations described herein.

Figure 2E:
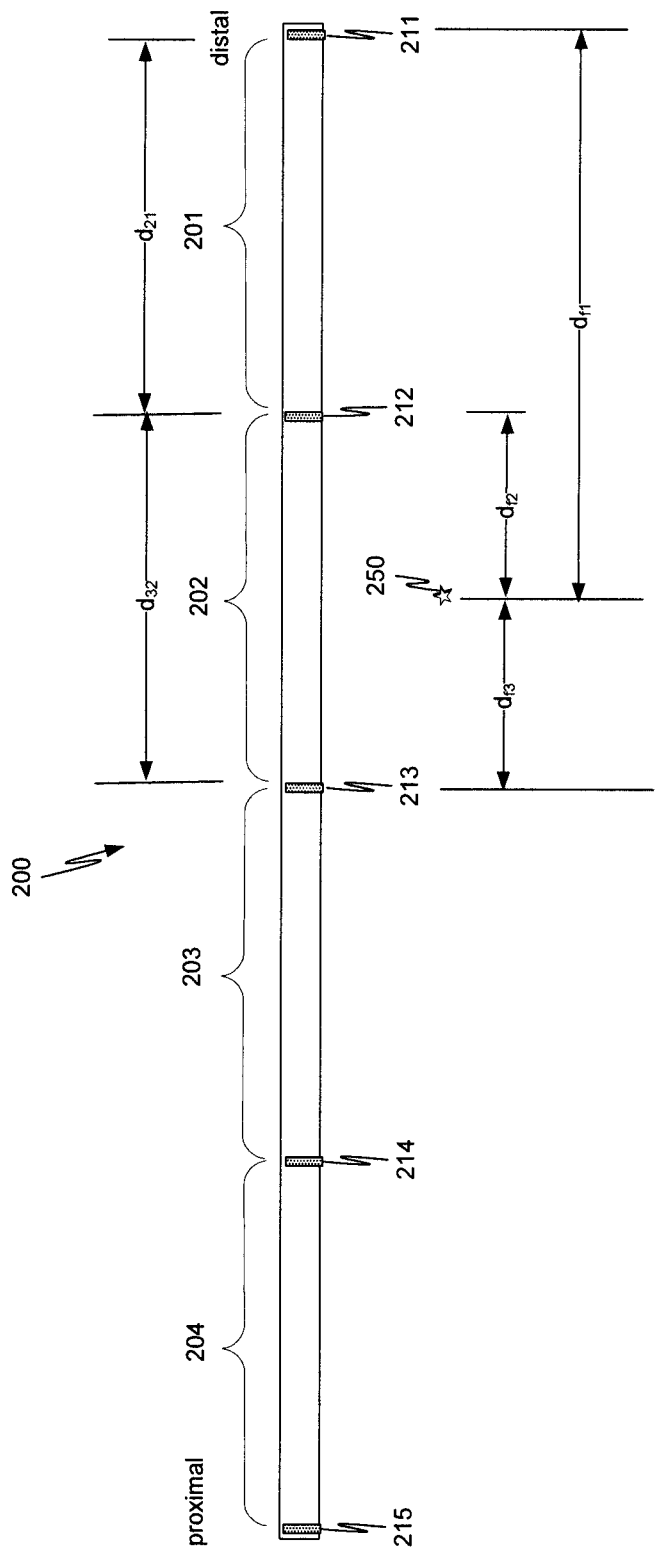

In the drawings, the first digit of a figure number indicates the figure in which the element with that figure number first appeared.

DETAILED DESCRIPTION

In one aspect, a steerable endoscope 100 (FIG. 1A) includes a plurality of segments 101-1, 101-2, . . . 101-n. Steerable endoscope 100 includes a plurality of global position sensors 111, 112, 113, . . . , 115, 116 fixed at known locations on steerable endoscope 100. Steerable endoscope 100 has a distal end 120, where the tip of steerable endoscope 100 is located, e.g., where the camera is located. The operator commands the position and orientation of the tip directly.

Herein, steerable endoscope 100 is an example of a steerable medical device that includes a plurality of segments. Accordingly, the description of steerable endoscope 100 is illustrative only and is not intended to be limiting to this specific steerable medical device.

Unlike prior art methods that required an external position sensor to determine the insertion depth of steerable endoscope 100, the measured locations of at least a pair of global position sensors in global position sensors 111, 112, 113, . . . , 115, 116 is used to determine the insertion depth of steerable endoscope 100 with respect to a foundation point 150. Foundation point 150 is initialized by an operator, such as a surgeon. The insertion depth, in turn, is used to determine the state of each segment that has passed foundation point 150, i.e., is distal to foundation point 150.

Foundation point 150 can be either internal or external to the body of the patient. In some procedures, foundation point 150 is a physiological reference position inside the body of the patient. However, in general, the location of foundation point 150 depends on the entry point for endoscope 100.

When the tip of endoscope 100 reaches a location that the operator wants to use as a foundation point, the operator selects the location of the tip as foundation point 150. Thus, the spatial location of foundation point 150 is the spatial location of the tip of endoscope 100 at the moment selected by the operator so that subsequent to that moment, the spatial location of foundation point 150 is known.

In this aspect, three states are defined for each segment of endoscope 100. The three states are passive, active, and articulating. Each segment has either an active or a passive state. In addition, a segment with an active state may also have an articulating state. Thus, in this aspect, a single segment may be in one of three conditions: a passive state, an active state, and dual active and articulating states. These states are illustrative only and are not intended to be limiting. In view of this disclosure, other states could be used.

In one aspect, segments completely proximal to foundation point 150 each have a passive state. Segments completely distal to foundation point 150 each have both an active state and an articulating state. A segment with a first portion distal to foundation point 150 and a second portion proximal to foundation point 150 can have either an active state alone, or this segment can have both an active state and an articulating state, as described more completely below.

FIGS. 1A to 1G show the change in foundation 150 relative to segments of endoscope 100, as endoscope 100 is moved into and out of the patient.

First segment 101-1 is an edge case and is always set to state active and state articulating because the tip of endoscope 100 is assumed to be active and articulating. Thus, in FIG. 1A, the number of active segments is one, and the number of articulating segments is one.

In FIG. 1B, endoscope 100 has been moved (e.g., inserted) so that the plane perpendicular to the insertion direction of endoscope 100 containing foundation point 150 is between global position sensor 112 and 113 (within segment 101-2). After the movement and before the conclusion of the processing of the new data set for the position in FIG. 1B, the two global position sensors bounding the most proximal currently active segment are global position sensors 111 and 112.

In FIG. 1C, endoscope 100 has been moved (e.g., withdrawn) so that the plane perpendicular to the insertion direction of endoscope 100 containing foundation point 150 is back in segment 101-1. After the movement and before the conclusion of the processing of the new data set for the position in FIG. 1C, the two global position sensors bounding the most proximal currently active segment are global position sensors 112 and 113. After this movement, foundation point 150 is bounded by global position sensors 111 and 112.

In FIG. 1D, endoscope 100 has been moved back to the same position as in FIG. 1B.

In FIG. 1E, endoscope 100 has been moved farther into the patient, but foundation point 150 is not past the half-way point of segment 101-2. After the movement and before the conclusion of the processing of the new data set for the position in FIG. 1E, the two global position sensors bounding the most proximal currently active segment are global position sensors 112 and 113. After this insertion movement, foundation point 150 is still bounded by global position sensors 112 and 113.

In FIG. 1F, endoscope 100 has been moved even farther into the patient so that foundation point 150 is positioned past the half-way point of segment 101-2. After the movement and before the conclusion of the processing of the new data set for the position in FIG. 1F, the two global position sensors bounding the most proximal currently active segment are global position sensors 112 and 113. After this insertion, foundation point 150 still is bounded by global position sensors 112 and 113.

In FIG. 1G, endoscope 100 has been withdrawn from the patient so that foundation point 150 is no longer positioned past the half-way point of segment 101-2. After the withdrawal and before the conclusion of the processing of the new data set for the position in FIG. 1G, the two global position sensors bounding the most proximal currently active segment are global position sensors 112 and 113. After this withdrawal, foundation point 150 is still bounded by global position sensors 112 and 113.

As endoscope 100 is moved as illustrated in FIGS. 1A to 1G, a processor determines the number of active and the number of articulating segments when a new set of global position data is received. The movements used are illustrative only and are not intended to be limiting.

Further, the determination of the numbers of active and articulating segments for each new set of global position data is illustrative only and is not intended to be limiting Depending on the frequency that a new set of global position data is generated, every new set of global position data may not be processed, e.g., every n-th new set might be processed where n is an integer number. As explained more completely below, in one aspect, an assumption is made about state transitions of segments in endoscope 100. The position of endoscope 100 relative to foundation point 150 should be updated using a new set of global position data at a frequency that supports this assumption.

For each new set of global position data processed, at least three distances are generated: a distance $d_{f(i-1)}$ from the distal global position sensor to the foundation point; a distance $d_{fi}$ from the proximal global position sensor to the foundation point; and a distance $d_{i(i-1)}$ between the proximal global position sensor and the distal global position sensor. In one aspect, the distal global position sensor and the proximal global position sensor used in the distance determinations are the proximal global position sensor and the distal global position sensor bounding the currently most proximal active segment. As used herein, an active segment is a segment with a state of active.

With respect to index i, the global position sensors are numbered starting at distal end 120 of endoscope 100 and proceeding towards proximal end 130 (FIG. 1A), with sensor 111 at distal end 120 of endoscope 100 having an index with a value of one (i=1). For a pair of global position sensors, the value of index i is the number of the proximal global position sensor in the pair.

Also, in this example, each segment is bounded by a pair of global position sensors. The total number of global position sensors is the number of segments plus one.

In one aspect, the positions of the global position sensors are sampled at least with a frequency such that at most a single state change occurs in only a single segment between adjacent sets of global position data that are analyzed. This means that if endoscope 100 has two segments articulating and two segments active, the next state of endoscope 100 is one of the following combinations: unchanged; two segments articulating and three segments active; and one segment articulating and two segments active, e.g., at most a single state change for a single segment has occurred between new sensor data sets that are analyzed.

Table 1 includes for the position of foundation point 150 in each of FIGS. 1B to 1G: the distal and proximal sensors of the most proximal active segment; the most proximal active segment; a result of the comparison of $d_{fi} < d_{f(i-1)}$; a result of the comparison of $d_{f(i-1)} > d_{i(i-1)}$ or $d_{fi} > d_{i(i-1)}$; and a command that is set to the motors of endoscope 100 as a result of the movement of endoscope 100.

TABLE 1

| Current FIG. | Distal Sensor i − 1 for most Proximal Active Segment (Ref No) | Proximal Sensor i for most Proximal Active Segment (Ref No) | Most Proximal Active Segment Prior to New Data (Ref No) | $d_{fi} < d_{f(i-1)}$ | $d_{f(i-1)} > d_{i(i-1)}$ (Seg. i Active) or $d_{fi} > d_{i(i-1)}$ (Seg. i Passive) | Motor Command |
|---|---|---|---|---|---|---|
| FIG. 1B | 1 (111) | 2 (112) | (101-1) | Don't Care | $d_{f1} > d_{21}$ True | Num. Act. = 2 Num. Art. = 1 |
| FIG. 1C | 2 (112) | 3 (113) | (101-2) | Don't Care | $d_{f3} > d_{32}$ True | Num. Act. = 1 Num. Art. = 1 |
| FIG. 1D | 1 (111) | 2 (112) | (101-1) | Don't Care | $d_{f1} > d_{21}$ True | Num. Act. = 2 Num. Art. = 1 |
| FIG. 1E | 2 (112) | 3 (113) | (101-2) | $d_{f3} < d_{f2}$ False | $d_{f3} > d_{32}$ False | Num. Act. = 2 Num. Art. = 1 |
| FIG. 1F | 2 (112) | 3 (113) | (101-2) | $d_{f3} < d_{f2}$ True | Don't Care | Num. Act. = 2 Num. Art. = 2 |
| FIG. 1G | 2 (112) | 3 (113) | (101-2) | $d_{f3} < d_{f2}$ False | Don't Care | Num. Act. = 2 Num. Art. = 1 |

With respect to FIG. 1B, the distances generated are a distance $d_{f1}$ from distal global position sensor 111 to the foundation point 150, a distance $d_{f2}$ from proximal global position sensor 112 to foundation point 150, and a distance $d_{21}$ between proximal global position sensor 112 and distal global position sensor ill. Foundation point 150 is bounded by a new set of global position sensors (sensors 113, 112), and so foundation point 150 is located in a new segment (segment 101-2). The insertion depth of endoscope 100 has increased relative to foundation point 150.

Distance $d_{f1}$ is greater than distance $d_{21}$, because foundation point 150 is farther from distal global position sensor 111 than the distance between proximal global position sensor 112 and distal global position sensor 111. Thus, the result of the comparison of $d_{f(i-1)} > d_{i(i-1)}$ is TRUE.

When the comparison of $d_{f(i-1)} > d_{i(i-1)}$ is TRUE, it is not necessary to determine whether the comparison of $d_{fi} < d_{f(i-1)}$ is TRUE, because of the limitation that at most a single state change occurs in only a single segment between adjacent sets of global position data. Thus, the comparison of $d_{fi} < d_{f(i-1)}$ for this movement of endoscope 100 is listed as a Don't Care condition in TABLE 1.

When the comparison of $d_{f(i-1)} > d_{i(i-1)}$ is TRUE, the segment (segment 101-2) proximal to the previously most proximal segment (segment 101-1) must be activated. Thus, the number of active segments is changed from one to two, and the number of articulating segments remains unchanged at one. When the controller for endoscope 100 (See FIG. 7)

receives the command with the number of active segments and the number of articulating segments, the controller activates the specified numbers starting with the most distal segment.

With respect to the movement of endoscope from the position shown in FIG. 1B to the position shown in FIG. 1C, the distances generated for the new set of global data are a distance $d_{f2}$ from distal global position sensor 112 to the foundation point 150, a distance $d_{f3}$ from proximal global position sensor 113 to foundation point 150, and a distance $d_{32}$ between proximal global position sensor 113 and distal global position sensor 112. Foundation point 150 is bounded by a new set of global position sensors (sensors 111, 112) and so foundation point 150 is located in a new segment (segment 101-1). The insertion depth of endoscope has decreased relative to foundation point 150.

Distance $d_{f3}$ is greater than distance $d_{32}$ because foundation point 150 is farther from proximal global position sensor 113 than the distance between distal global position sensor 112 and proximal global position sensor 113. Thus, the result of the comparison of $d_{fi}>d_{i(i-1)}$ is TRUE.

When the comparison of $d_{fi}>d_{i(i-1)}$ is TRUE, it is not necessary to determine whether the comparison of $d_{fi}<d_{f(i-1)}$ is TRUE, because of the limitation that at most a single state change occurs in only a single segment between adjacent sets of global position data. Thus, the comparison of $d_{fi}<d_{f(i-1)}$ for this movement of endoscope 100 is listed as a Don't Care condition in TABLE 1.

When the comparison of $d_{fi}>d_{i(i-1)}$ is TRUE, the currently most proximal active segment (segment 101-2) must be made passive. Thus, the number of active segments is changed from two to one, and the number of articulating segments remains unchanged at one.

The movement of endoscope 100 from FIG. 1C to FIG. 1D is the same as that in FIG. 1B. Thus, when endoscope 100 is inserted farther into the patient as represented by the transition for FIG. 1C to 1D, the number of active segments is changed from one to two, and the number of articulating segments remains unchanged at one.

With respect to the movement of endoscope from the position shown in FIG. 1D to the position shown in FIG. 1E, the distances generated for the new set of global data are a distance $d_{f2}$ from distal global position sensor 112 to the foundation point 150, a distance $d_{f3}$ from proximal global position sensor 113 to foundation point 150, and a distance $d_{32}$ between proximal global position sensor 113 and distal global position sensor 112. Foundation point 150 is not bounded by a new set of global position sensors and so foundation point 150 is not located in a new segment.

Distance $d_{f3}$ is greater than distance $d_{f2}$, because distal global position sensor 112 is closer to foundation point 150 than proximal global position sensor 113. Thus, the result of the comparison of $d_{fi}<d_{f(i-1)}$ is FALSE.

However, since most proximal active segment 101-2 does not have state articulating, this comparison could be true because the foundation point remained in the same segment or because the foundation point is now located in a more distal segment. Thus, to determine whether the foundation point is located in the more distal segment, distance $d_{f3}$ is compared to distance $d_{32}$. Since the foundation point remained in the same segment in FIG. 1E, this comparison is FALSE.

Thus, when the result of the comparison of $d_{fi}<d_{f(i-1)}$ is FALSE and the most proximal segment with state active does not have state articulating and the result the comparison of $d_{fi}>d_{i(i-1)}$ is also FALSE, the state of the most proximal active segment 101-2 remains active. Thus, the number of active segments is unchanged and remains at two. The number of articulating segments remains at one.

With respect to the movement of endoscope 100 from the position shown in FIG. 1E to the position shown in FIG. 1F, the distances generated for the new set of global data are a distance $d_{f2}$ from distal global position sensor 112 to the foundation point 150, a distance $d_{f3}$ from proximal global position sensor 113 to foundation point 150, and a distance $d_{32}$ between proximal global position sensor 113 and distal global position sensor 112. Foundation point 150 is not bounded by a new set of global position sensors and so foundation point 150 is not located in a new segment.

Distance $d_{f3}$ is less than distance $d_{f2}$, because proximal global position sensor 113 is closer to foundation point 150 than distal global position sensor 112. Thus, the result of the comparison of $d_{fi}<d_{f(i-1)}$ is TRUE.

When the comparison of $d_{fi}<d_{f(i-1)}$ is TRUE, it is not necessary to determine the outcome of the comparison of $d_{f(i-1)}>d_{i(i-1)}$ or the outcome of the comparison of $d_{fi}>d_{i(i-1)}$ because of the limitation that at most a single state change occurs in only a single segment between adjacent sets of global position data. Thus, the comparisons of $d_{f(i-1)}>d_{f(i-1)}$ and $d_{fi}>d_{i(i-1)}$ for this movement of endoscope 100 are listed as a Don't Care condition in TABLE 1.

When comparison of $d_{fi}<d_{f(i-1)}$ is TRUE, the state of most proximal active segment 101-2 remains active, and the state of most proximal active segment 101-2 also is changed to articulating if that segment does not already have state articulating. Thus, the number of active segments is unchanged, and remains at two. The number of articulating segments is changed from one to two.

When endoscope 100 moves so that foundation point 150 remains in segment 101-2, and the comparison of $d_{fi}<d_{f(i-1)}$ is TRUE, the state of current segment 101-2 remains unchanged. The number of active segments is unchanged and remains at two. The number of articulating segments also is unchanged and remains at two.

However, if endoscope 100 moves from the position shown in FIG. 1F to the position shown in FIG. 1G, the distances generated for the new set of global data are a distance $d_{f2}$ from distal global position sensor 112 to the foundation point 150, a distance $d_{f3}$ from proximal global position sensor 113 to foundation point 150, and a distance $d_{32}$ between proximal global position sensor 113 and distal global position sensor 112. Foundation point 150 is not bounded by a new set of global position sensors, and so foundation point 150 is not located in a new segment.

Distance $d_{f3}$ is greater than distance $d_{f2}$, because distal global position sensor 112 is closer to foundation point 150 than proximal global position sensor 113. Thus, the result of the comparison of $d_{fi}<d_{f(i-1)}$ is FALSE.

When the result of the comparison of $d_{fi}<d_{f(i-1)}$ is FALSE and the most proximal segment with state active also has state articulating, it is not necessary to determine the outcome of the comparison of $d_{f(i-1)}>d_{i(i-1)}$ or the outcome of the comparison of $d_{fi}>d_{i(i-1)}$ because of the limitation that at most a single state change occurs in only a single segment between adjacent sets of global position data. Thus, the comparisons of $d_{f(i-1)}>d_{i(i-1)}$ and $d_{fi}>d_{i(i-1)}$ for this movement of endoscope 100 are listed as a Don't Care condition in TABLE 1.

Thus, when the result of the comparison of $d_{fi}<d_{f(i-1)}$ is FALSE and the most proximal segment with state active also has state articulating, the state of the most proximal active segment 101-2 remains active and the state of articulating is dropped. Thus, the number of active segments is unchanged and remains at two. The number of articulating segments is changed from two to one.

The above examples assumed that the first time endoscope 100 moved so that foundation point 150 was bounded by a new segment, the state of the new segment was changed to active. However, such movement could be an anomaly. If foundation point 150 is very close to the edge of a region, force on endoscope 100, patient breathing, or some other external interaction could cause foundation point 150 to be in a different region for a long enough period that a segment would have time to transition to a new state.

To prevent this undesirable motion that can result in oscillatory state changes, hysteresis is added to change the calculated position of foundation point 150. For example, not only must distance $d_{f(i-1)}$ be greater than distance $d_{fi}$ for example, but also distance $d_{f(i-1)}$ must be greater than distance $d_{fi}$ by some margin, e.g., one centimeter. This condition inhibits segments from transitioning state without significant endoscope motion.

Also, low pass filtering could be used for the sets of global position data so that transient data does not affect the determination of the number of active segments and the number of articulating segments. In one aspect, as described below, the low pass filtering is implemented by requiring a fixed number of datasets to give the same result before that result is implemented.

The information in TABLE 1 could be implemented, for example, as a look-up table. However, in one aspect, a method is implemented on a processor for controlling the number of active segment and the number of articulating segments as a medical device is moved relative to a foundation point.

In one aspect, the method uses the locations of the global position sensors to calculate the distances that were described above. In another aspect, the method uses a kinematic model to generate locations for each link in a segment. The locations are connected to generate a centerline representation of the endoscope. The foundation point is fitted to the centerline representation and the insertion depth is the distance along the centerline representation distal to the foundation point.

Each of these methods is considered more completely below. Both methods effectively determine the number of active segments and the number of articulating segments relative to the foundation point.

To demonstrate aspects of one method, a steerable endoscope 200 (FIG. 2A), sometimes referred to as endoscope 200, is considered. Endoscope 200 is similar to endoscope 100, but, in this example, endoscope 200 includes four segments 201 to 204. Global position sensors 211, 215 are provided at distal end 220 and proximal end 230 of steerable endoscope 200, respectively. While not shown in FIG. 2A, the tip of endoscope is located at distal end 220. Global position sensors 212, 213, 214, are also provided, one between each segment. Using global position sensors 211 to 215, the start and end spatial coordinates of each segment can be measured using conventional techniques, e.g., radio frequency, electromagnetic, or optical techniques, and so are known.

The number of segments is illustrative only and is not intended to be limiting to the specific number described herein. Also, the use of global position sensors is illustrative of use of sensors relative to the body of the patient that provide information on position data of at least one segment relative to the foundation point. Thus, the description of global position sensors is illustrative only and is not intended to be limiting.

As an operator starts to insert endoscope 200 into a patient, method 300 (FIGS. 3A and 3B) is started. As explained more completely below, method 300 analyzes the measured global position for at least a pair of global sensors 211 to 215 relative to foundation position 250 and each other. Method 300 requires little processing, and may be useful for simpler modes of endoscope operation as well as other medical devices having articulatable segments.

As used herein, global position and global position data refer to position measurement or tracking of endoscope segments or endoscope links using a reference location, foundation point 250 in this example, that is the same for all segments and links. This is contrasted with local position or shape measurement methods that determine the position or shape of each segment or link relative to other segments or links.

In method 300, a segment is active if any part of the segment has passed foundation point 250. The segment is active and articulating if half or more of the segment has passed foundation point 250. The use of the half-way point to change the state of a segment from active to active and articulating is illustrative only and is not intended to be limiting. In view of this disclosure, one knowledgeable in the field can select criteria relative to the foundation point for sending segments active and articulating based on the particular steerable medical device and procedure of interest. Irrespective of the criteria, the position of foundation point 250 is known.

In FIGS. 2B to 2E, selected positions of endoscope 200 are considered to demonstrate method 300. Typically, following INITIALIZE operation 301 (FIG. 3A) and FOUNDATION POINT INITIALIZED check operation 302, ACTIVE/PASSIVE process 390 (shown bounded by dashed lines in FIGS. 3A and 3B) is repeated each time global position data 303A is updated. Thus, ACTIVE/PASSIVE process 390 may be performed more frequently than indicated by the endoscope positions in FIGS. 2B to 2E. These positions were selected to demonstrate elements of process 390 and so are illustrative only and are not intended to be limiting.

Initially, in method 300, INITIALIZE operation 301 initializes elements used in method 300. For example, a value of a number of segments active variable NumAct is set to one, a value of a number of segments articulating variable NumArt is set to one, and a value of a maximum count variable countMax is set to five.

Upon completion of INITIALIZE operation 301, method 300 remains in FOUNDATION POINT INITIALIZED check operation 302, until foundation point 250 is initialized. When the tip of endoscope 200 reaches a point that the operator wants to use as a foundation point, the operator takes an action that initializes foundation point 250 as the current location of the tip. The particular action taken by the operator is not essential so long as the system recognizes the action, e.g., pushing a button, as direction to use the current tip position of endoscope 200 as foundation point 250.

Also, check operation 302 should not be interpreted as requiring polling. Check operation 302, for example, could be implemented as part of an event handler and when a foundation point initialized event occurs, method 390 is launched.

Upon initialization of foundation point 250, active/passive method 390 is launched and processing transfers from FOUNDATION POINT INITIALIZED check operation 302 to GENERATE DISTANCES TO FOUNDATION POINT operation 303. Operation 303 accesses the location of foundation point 250 and the global position data for at least the pair of global position sensors bounding the currently most proximal active segment. Operation 303 generates the distance from each of these global position sensors to foundation point 250.

For the example, in FIG. 2B, operation 303 generates distance $d_{f1}$ from distal global position sensor 211 to foundation point 250, and generates distance $d_{f2}$ from proximal global position sensor 212 to foundation point 250. Also, the distance from global position sensor 211 to global position sensor 212 is generated and is shown in FIG. 2B as distance $d_{21}$. Upon completion of operation 303 processing transfers to FOUNDATION POINT NEAREST TIP check operation 304.

FOUNDATION POINT NEAREST TIP check operation 304 determines whether foundation point 250 is closest to the most proximal global position sensor 211, e.g., closest to the tip of endoscope 200. The segment of endoscope 200 that includes the tip is expected to be active and articulating and so method 390 must preserve this characteristic.

In one aspect, check operation 304 determines whether distance $d_{f1}$ is less than distance $d_{f2}$, and whether the value of number of segments active variable NumAct is equal to one. If both these conditions are true, foundation point 250 is nearest the tip and check operation 304 transfers processing to SET TEMPORARY ACTIVE AND ARTICULATING operation 305. If either or both of the conditions are not true, check operation 304 transfers processing to INITIALIZE INDEX operation 306.

In the example of FIG. 2B, distance $d_{f1}$ is less than distance $d_{f2}$ and so the first condition is true. Also, the value of number of segments active variable NumAct is equal to one and so the second condition is true. Thus, foundation point 250 is nearest the tip, as shown in FIG. 2B, and check operation 304 transfers processing to SET TEMPORARY ACTIVE AND ARTICULATING operation 305.

SET TEMPORARY ACTIVE AND ARTICULATING operation 305 sets a value of a temporary active segments variable tempAct to one and a value of a temporary articulating segments variable tempArt to one. Operation 305 transfers processing to GO ACTIVE/PASSIVE operation 318 (FIG. 3B).

GO ACTIVE/PASSIVE operation 318 sets the value of number of segments active numAct to the value of temporary active segments variable tempAct. Operation 318 also sets the value of number of segments articulating numArt to the value of temporary articulating segments variable tempArt. Operation 318 then sends a command to the motors for endoscope 200 that configures the number of articulating segments of endoscope 200 to be the value of number of segments articulating numAct, and configures the number of active segments of endoscope 200 to be the value of number of segments active numAct. Thus, operation 318 sends a command to a controller to configure endoscope 200 to have number of segments articulating numAct and number of segments active numAct.

Figure 3A:
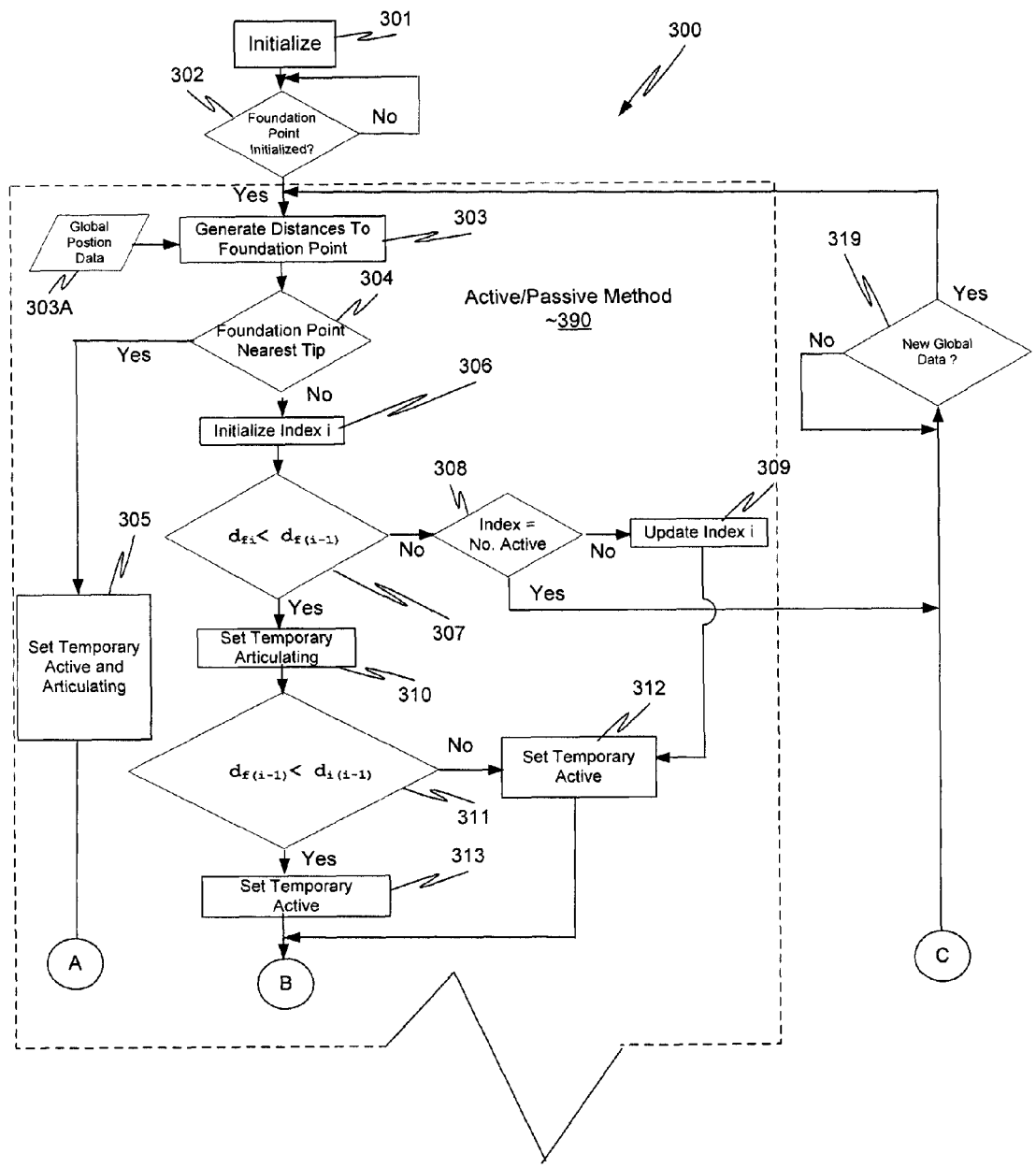
FIGS. 3A and 3B are a process flow diagram for one method of determining a number of active segments and a number of articulating segments for each of the configurations illustrated in FIGS. 2B to 2E.
Figure 3B:
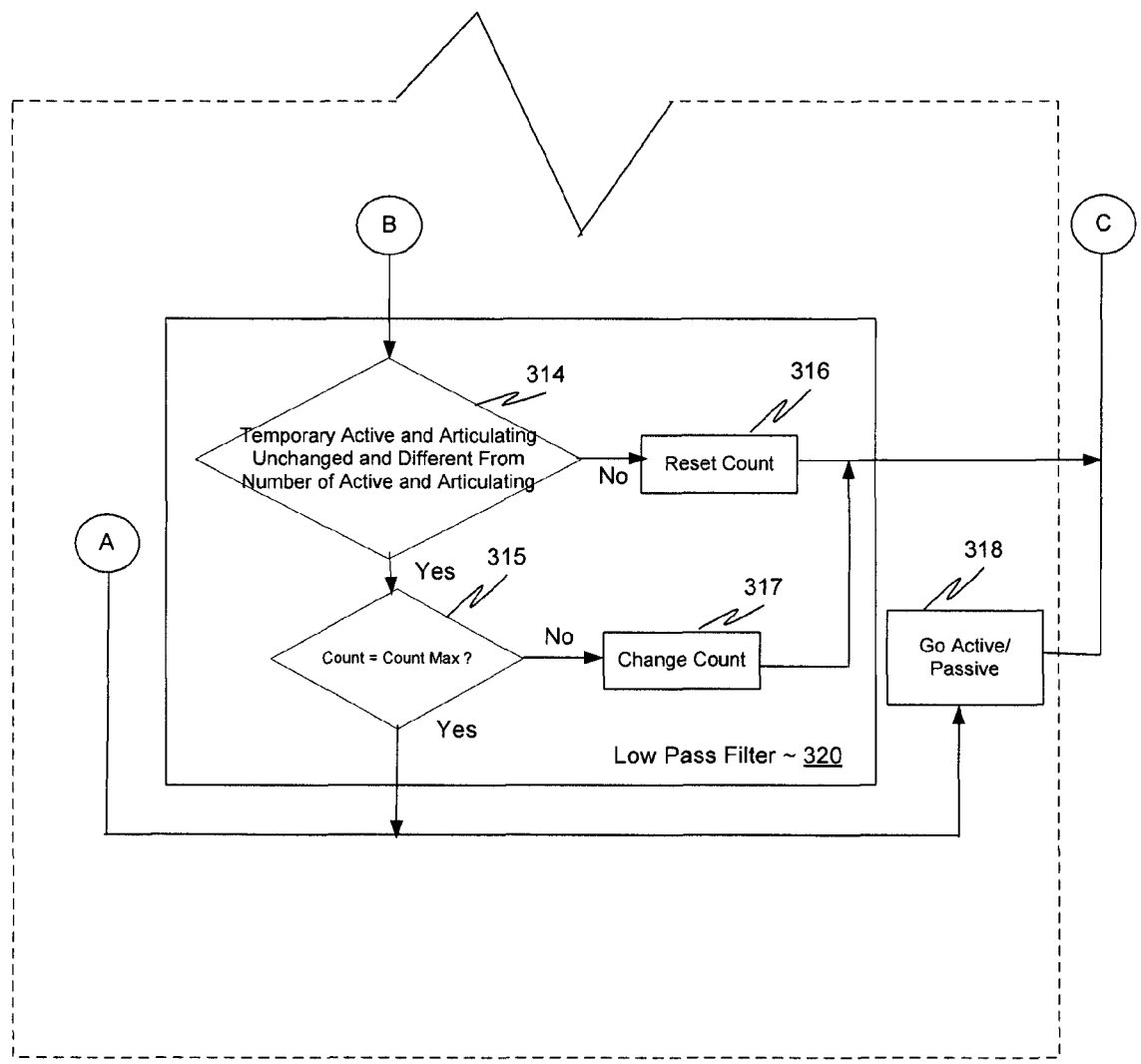

Upon completion, GO ACTIVE/PASSIVE operation 318 (FIG. 3B) transfers to NEW GLOBAL DATA check operation 319 (FIG. 3A). When a new set of global position data is available, check operations transfers to GENERATE DISTANCES TO FOUNDATION POINT operation 303 and ACTIVE/PASSIVE method 390 is started again. Check operation 319 can be configured to transfer to method 390 for other than every new set of global position data. Method 390 is initiated when a new set of global position data is saved by check operation 319, e.g., when a new set of global position data is received.

Turning now to FIG. 2C and considering the new global data set to represent the configuration illustrated in FIG. 2C, operation 303 generates distance $d_{f1}$ from distal global position sensor 211 to foundation point 250, and generates distance $d_{f2}$ from proximal global position sensor 212 to foundation point 250. The distance from global position sensor 211 to global position sensor 212 also is generated and is shown in FIG. 2B as distance $d_{21}$. Upon completion of operation 303 processing transfers to FOUNDATION POINT NEAREST TIP check operation 304.

As described above, FOUNDATION POINT NEAREST TIP check operation 304 determines whether foundation point 250 is closest to the most proximal global position sensor 211, e.g. closest to the tip of endoscope 200. In the example of FIG. 2C, distance $d_{f1}$ is greater than distance $d_{f2}$ and so the first condition is not true. The value of number of segments active variable NumAct is equal to one and so the second condition is true. Thus, foundation point 250 is not nearest the tip, as shown in FIG. 2C, and check operation 304 transfers to INITIALIZE INDEX operation 306.

INITIALIZE INDEX operation 306 sets the value of index i to the value of number of segments active variable NumAct plus one. Thus, for this example, index i has a value of two. Upon completion, INITIALIZE INDEX operation 306 transfers processing to $d_{fi} < d_{f(i-1)}$ check operation 307.

In one aspect, $d_{fi} < d_{f(i-1)}$ check operation 307 determines whether foundation point 250 is closer to the distal global position sensor i than to proximal global position sensor (i−1). If the foundation point is closer to distal global position sensor i than to proximal global position sensor (i−1), check operation 307 transfers processing to SET TEMPORARY ARTICULATING operation 310 and otherwise to INDEX EQUALS NUMBER OF ACTIVE check operation 308.

In FIG. 2C with the value of index i equal to two, distance $d_{f2}$ is less than distance $d_{f1}$, i.e., foundation point 250 is closer to proximal global position sensor 212 for segment 201 than to distal global position sensor 211. Thus, check operation 307 transfers processing to SET TEMPORARY ARTICULATING operation 310.

SET TEMPORARY ARTICULATING operation 310 sets the value of temporary articulating segments variable tempArt to the value of index i minus one. In this example, index i has a value of two and so the value of temporary articulating segments variable tempArt is one. Upon completion, SET TEMPORARY ARTICULATING operation 310 transfers processing to $d_{f(i-1)} < d_{i(i-1)}$ check operation 311.

$d_{f(i-1)} < d_{i(i-1)}$ check operation 311 determines whether distance $d_{f(i-1)}$ from the foundation point to the distal global position sensor is less than the distance between proximal and distal global position sensors $d_{i(i-1)}$. If distance $d_{f(i-1)}$ is greater than distance $d_{i(i-1)}$, check operation 311 transfers to SET TEMPORARY ACTIVE operation 312, which in turn sets the value of temporary active segments variable tempAct to the value of index i. If distance $d_{f(i-1)}$ is less than distance $d_{i(i-1)}$, check operation 311 transfers to SET TEMPORARY ACTIVE operation 312, which in turn sets the value of temporary active segments variable tempAct to the value of index i minus one. Both SET TEMPORARY ACTIVE operation 312, and SET TEMPORARY ACTIVE operation 313 transfer processing to low pass filter 320 (FIG. 3B).

Continuing with the example of FIG. 2C, index i has the value two and so the distances of interest are distances $d_{f1}$ and $d_{21}$. Distance $d_{f1}$ from global position sensor 211 to foundation point 250 is less than distance $d_{21}$ between global position sensor 211 and global position sensor 212. It is not necessary to activate another segment at this time. Thus, check operation 311 transfers to SET TEMPORARY ACTIVE operation 313. In this example, index i has a value of two and so the value of temporary active segments variable tempArt is one, i.e., is maintained at the same value.

In low pass filter 320 (FIG. 3B), TEMPORARY ACTIVE AND ARTICULATING UNCHANGED AND DIFFERENT FROM NUMBER OF ACTIVE AND ARTICULATING check operation 314 is used in combination with check operation 315 to assure that transient conditions do not result in changing the number of articulating and the number of active segments in endoscope 200.

Check operation 314 determines whether a change in the number of active segments or the number of articulating segments has occurred. Check operation 315 assures that a predefined number of samples of global position data, i.e., the value of maximum count variable countMax, gives the same change before the number of articulating and active segments in endoscope 200 is changed.

Specifically, TEMPORARY ACTIVE AND ARTICULATING UNCHANGED AND DIFFERENT FROM NUMBER OF ACTIVE AND ARTICULATING check operation 314 compares the value of temporary active segments variable tempAct with a saved value of that variable. Check operation 314 also compares the value of temporary articulating segments variable tempArt with a saved value of that variable. If either comparison shows a change, i.e., the values are not equal, check operation 314 transfers processing to RESET COUNT operation 316.

Conversely, if both comparisons show that no change has occurred in the value of either variable tempAct or variable tempArt, check operation 314 compares the value of temporary active segments variable tempAct to the value of number of segments active variable numAct and compares the value of temporary articulating segments variable tempArt to the value of number of segments articulating variable numArt. If both comparisons are true, i.e., the values are equal, check operation 314 transfers processing to RESET COUNT operation 316. If either of the comparisons is not true, at least one set of the values are not equal, check operation 314 transfers processing to COUNT EQUAL COUNT MAXIMUM check operation 315 that is described more completely below.

For the example of FIG. 2C, check operation 314 determines that the values of both temporary active segments variable tempAct and temporary articulating segments variable tempArt are unchanged. However, the value of temporary active segments variable tempAct equals the value of number of segments active variable numAct and the value of temporary articulating segments variable tempArt equals the value of number of segments articulating variable numArt. Thus, check operation 314 transfers processing to RESET COUNT operation 316.

RESET COUNT operation 316 sets a count variable COUNT to zero, in this example. RESET COUNT operation 316 transfers processing to NEW GLOBAL CHECK operation 319 (FIG. 3A), which was described above.

Turning now to FIG. 2D, prior to endoscope 200 being moved to the location shown in FIG. 2D, endoscope 200 had been moved from the location shown in FIG. 2C so that foundation point 250 was proximal to global position sensor 212. As a result of this prior move, the state of segment 202 was set to active and the number of segments active variable numAct was set to two. After the prior move, endoscope 200 was moved to the position shown in FIG. 2D and a new set of global position data has been received. Since segment 202 is active when the new set of global position data was received, number of segments active variable numAct has the value two and number of segments articulating variable numArt has the value one.

In this example, operation 303 distance $d_{f2}$ from global position sensor 212 to foundation point 250; and generates distance $d_{f3}$ from global position sensor 213 to foundation point 250. Distance $d_{32}$ from global position sensor 213 to global position sensor 212 is also generated. Upon completion of operation 303 processing transfers to FOUNDATION POINT NEAREST TIP check operation 304.

As described above, FOUNDATION POINT NEAREST TIP check operation 304 determines whether foundation point 250 is closest to the most proximal global position sensor 211, e.g. closest to the tip of endoscope 200. In the example of FIG. 2D, distance $d_n$ is greater than distance $d_u$ and so the first condition is not true. The value of number of segments active variable NumAct is not equal to one. Thus, foundation point 250 is not nearest the tip, as shown in FIG. 2D, and check operation 304 transfers to INITIALIZE INDEX operation 306.

Note that for ease of illustration FOUNDATION POINT NEAREST TIP check operation 304 is considered in each iteration of method 300 as endoscope 200 is moved. However, in one aspect, check operation 304 is not performed after the pass through method 300 that sets the state of the first segment to active and articulating, because after that pass, endoscope 200 is known to have the first segment set to state active and articulating. Thus, the consideration of FOUNDATION POINT NEAREST TIP check operation 304 simply demonstrates that it is unnecessary to consider operation 304 in iterations after the edge case has been handled.

INITIALIZE INDEX operation 306 sets the value of index to the value of number of segments active variable NumAct plus one. Thus, for this example, index i has a value of three. Upon completion, INITIALIZE INDEX operation 306 transfers processing to $d_{fi} < d_{f(i-1)}$ check operation 307.

In FIG. 2D with index i equal to three, distance $d_{f3}$ is greater than distance $d_{f2}$, i.e., foundation point 250 is closer to distal global position sensor 212 for segment 202 than to proximal global position sensor 213. Thus, check operation 307 transfers processing to INDEX EQUALS NUMBER OF ACTIVE CHECK operation 308.

INDEX EQUALS NUMBER OF ACTIVE CHECK operation 308 compares the value of index i with the value of number of segments active variable NumAct. At this time, index i equals three and the value of number of segments active variable NumAct is two. Thus, the comparison is false, and check operation 308 transfers processing to UPDATE INDEX operation 309.

UPDATE INDEX operation 309, in this example, decrements the value of index i. Thus, index i now has a value of two. UPDATE INDEX operation 309 transfers processing to SET TEMPORARY ACTIVE operation 312.

SET TEMPORARY ACTIVE operation 312 sets the value of temporary active segments variable tempAct to the value of index i. In this example, index i has a value of two and so the value of temporary active segments variable tempArt is two. Upon completion, SET TEMPORARY ACTIVE operation 312 transfers processing to TEMPORARY ACTIVE AND ARTICULATING UNCHANGED AND DIFFERENT FROM NUMBER OF ACTIVE AND ARTICULATING check operation 314.

In the example of FIG. 2D, check operation 314 determines that the values of temporary active segments variable tempAct and temporary articulating segments variable tempArt are unchanged. However, the value of temporary active segments variable tempAct equals the value of number of segments active variable numArt and the value of temporary articulating segments variable tempArt equals the value of number of segments articulating variable numArt. Thus, check operation transfers processing to RESET COUNT operation 316 that was described above.

Turning now to FIG. 2E, endoscope 200 has moved so that the insertion depth has increased and a new set of global position data has been received. Recall number of segments active variable numAct has the value two. However, foundation point 250 has just passed the center point of segment 202 and the value of number of segments articulating numArt is still one.

For the configuration in FIG. 2E, operation 303 generates distance $d_{f2}$ from global position sensor 212 to foundation point 250, and generates distance $d_{f3}$ from global position sensor 213 to foundation point 250. Distance $d_{32}$ from global position sensor 213 to global position sensor 212 is also generated. Upon completion of operation 303 processing transfers to FOUNDATION POINT NEAREST TIP check operation 304.

As described above, FOUNDATION POINT NEAREST TIP check operation 304 determines whether foundation point 250 is closest to the most proximal global position sensor 211, e.g. closest to the tip of endoscope 200. In the example of FIG. 2E, distance $d_{f1}$ is greater than distance $d_{f2}$ and so the first condition is not true. The value of number of segments active variable NumAct is not equal to one. Thus, foundation point 250 is not nearest the tip, as shown in FIG. 2E, and check operation 304 transfers to INITIALIZE INDEX operation 306.

INITIALIZE INDEX operation 306 sets the value of index i to the value of number of segments active variable NumAct plus one. Thus, for this example, index i has a value of three. Upon completion, INITIALIZE INDEX operation 306 transfers processing to $d_{fi}<d_{f(i-1)}$ check operation 307.

In FIG. 2E with the value of index i equal to three, distance $d_{f3}$ is less than distance $d_{f2}$, i.e., foundation point 250 is closer to proximal global position sensor 213 for segment 202 than to distal global position sensor 212. Thus, check operation 307 transfers processing to SET TEMPORARY ARTICULATING operation 310.

SET TEMPORARY ARTICULATING operation 310 sets the value of temporary articulating segments variable tempArt to the value of index i minus one. In this example, index i has a value of three and so the value of temporary articulating segments variable tempArt is two. Upon completion, SET TEMPORARY ARTICULATING operation 310 transfers processing to $d_{f(i-1)}<d_{i(i-1)}$ check operation 311.

Continuing with the example of FIG. 2E, index i has the value three and so the distances of interest in check operation 311 are distances $d_{f2}$ and $d_{32}$. Distance $d_{f2}$ from global position sensor 212 to foundation point 250 is less than distance $d_{32}$ between global position sensor 213 and global position sensor 212.

Operation 311 transfers to SET TEMPORARY ACTIVE operation 313. SET TEMPORARY ACTIVE operation 313 sets the value of temporary active segments variable tempAct to the value of index i minus one. In this example, index i has a value of three and so the value of temporary active segments variable tempArt is two. Upon completion, SET TEMPORARY ACTIVE operation 313 transfers processing to TEMPORARY ACTIVE AND ARTICULATING UNCHANGED AND DIFFERENT FROM NUMBER OF ACTIVE AND ARTICULATING check operation 314.

In the example of FIG. 2E, check operation 314 determines that the value of temporary active segments variable tempAct is unchanged, but the value of temporary articulating segments variable tempArt has changed. The value of temporary active segments variable tempAct equals the value of number of segments active variable numAct, but the value of temporary articulating segments variable tempArt does not equal the value of number of segments articulating variable numArt. Thus, check operation 314 transfers processing to COUNT EQUALS COUNT MAXIMUM check operation 315.

COUNT EQUALS COUNT MAXIMUM check operation 315 compares the value of variable COUNT with the value of maximum count variable countMax. The value of variable COUNT depends on the number of times in a row that processing has reached check operation 315. If variable COUNT has any value less than the value of maximum count variable countMax, check operation 315 transfers processing to CHANGE COUNT operation 317, which increments the value of variable COUNT, and transfers to NEW GLOBAL DATA check operation 319 that was described above. Conversely, if the value of variable COUNT equals the value of maximum count variable countMax, check operation 315 transfers processing to GO ACTIVE/PASSIVE operation 318.

GO ACTIVE/PASSIVE operation 318 sets the value of number of segments active numAct to the value of temporary active segments variable tempAct. Operation 318 also sets the value of number of segments articulating numArt to the value of temporary articulating segments variable tempArt. Operation 318 then sends a command to the motors for endoscope 200 that configures the number of articulating segments of endoscope 200 to be the value of number of segments articulating numAct, and configures the number of active segments of endoscope 200 to be the value of number of segments active numAct. Thus, operation 318 sends a command to a controller to configure endoscope 200 to have the number of segments articulating numAct and the number of segments active numAct. Upon completion, GO ACTIVE/PASSIVE operation 318 transfers to NEW GLOBAL DATA check operation 319 that was described above.

In method 390, a command was not sent to the motors of endoscope 200 until the same number of active segments and the same number of articulating segments were found in a predetermined number of consecutive sets of global position data. If low pass filter 320 were eliminated, each iteration of method 390 would send a command to the motors of endoscope 200. However, sensor noise might cause segments to transition between active and passive states or articulating and non-articulating states often. To prevent excessive transitions, the low pass filter was implemented before sending a new command to the motors. As illustrated in process 390, multiple (for example five) consecutive sensor readings are required to produce the same command before the command is sent to the actuators If the foundation point is very close to the edge of a region, force on the endoscope, patient breathing, or some other external interaction could move a segment beyond the foundation point for a long enough period that the segment would have time to transition state. To prevent this undesirable motion, hysteresis is added to change the calculated position of the foundation point. For example, in check operation 307 not only must distance $d_{f(i-1)}$ be greater than distance $d_{fi}$ for example, but also distance $d_{f(i-1)}$ must be greater than distance $d_{fi}$ by some margin, e.g., one centimeter. A similar margin can be used in check operation 311. Use of hysteresis, as defined herein, inhibits segments from transitioning state without significant motion.

Active/Passive method 390 looked only at the positions of position sensors relative to a foundation point and each other. Another method, as described below, uses the position and orientation of each of the position sensors to find the best configuration fit to the kinematics of endoscope 200.

As described above, in one aspect, steerable endoscope 200, sometimes referred to as endoscope 200, includes four segments 201 to 204. As illustrated in FIG. 4A, steerable endoscope 400 also includes four segments 401 to 404 and each segment includes eight links.

Global position sensors 411, 415 are provided at distal end 420 and proximal end 430 of steerable endoscope 400, respectively. While not shown in FIG. 4A, the tip of endoscope is located at distal end 420. A global position sensor 412, 413, 414, is also provided between each segment so that each segment is bounded by a pair of global position sensors, in this embodiment. Using global position sensors 411 to 415, the start and end spatial coordinates of each segment can be measured using conventional techniques, e.g., radio frequency, electromagnetic, or optical techniques, and so are known. The number of segments is illustrative only and is not intended to be limiting to the specific number described herein.

FIG. 4B is a more detailed diagrammatic drawing of a kinematic model for a representative segment j of steerable endoscope 400 with an indication of the link angle and the appropriate roll matrix. Here, j is an integer ranging from one to four for segments 401 to 404, respectively. In determining the orientation of each of the links, a transform is defined for each link.

The transform for the pitch-links is:

$$T_{xi} = \begin{bmatrix} R_x(\theta_{xi}) & \begin{pmatrix} 0 \\ 0 \\ -a(xi) \end{pmatrix} \\ 0 & 1 \end{bmatrix}, i = 1 \text{ to } 4$$

a(xi) is the displacement for link xi; and $$R_x(\theta_{xi}) = \begin{bmatrix} 1 & 0 & 0 \\ 0 & \cos(\theta_{xi}) & -\sin(\theta_{xi}) \\ 0 & \sin(\theta_{xi}) & \cos(\theta_{xi}) \end{bmatrix}$$

The transform for the yaw-links is:

$$T_{yi} = \begin{bmatrix} R_y(-\theta_{yi}) & \begin{pmatrix} 0 \\ 0 \\ -a(yi) \end{pmatrix} \\ 0 & 1 \end{bmatrix}, i = 1 \text{ to } 4$$

a(yi) is the displacement for link yi $$R_y(-\theta_{yi}) = \begin{bmatrix} \cos(\theta_{yi}) & 0 & -\sin(\theta_{yi}) \\ 0 & 1 & 0 \\ \sin(\theta_{yi}) & 0 & \cos(\theta_{yi}) \end{bmatrix}$$

In the transform there are eight variables, but the global position data has only six coordinates. The angle of rotation for each transform $T_i$ is estimated with a constrained minimization. The constraint, in one aspect, is:

$$^{i-1}_iT = T_{y1}T_{x1}T_{y2}T_{x2}T_{y3}T_{x3}T_{y4}T_{x4}$$

where $^{i-1}_iT$ is the transform from global position sensor i at the proximal end of segment j to global position sensor (i−1) at the distal end of segment j. Transform $^{i-1}_iT$ for segment j is known based on the global position data, e.g., the relative positions and orientations, of two adjacent global position sensors i, (i−1).

With respect to index i, the global position sensors are numbered starting at distal end 420 of endoscope 400 and proceeding towards proximal end 430, with sensor 411 at distal end of endoscope having index one. For a pair of global position sensors, the value of index i is the number of proximal global position sensor in the pair.

A minimized cost function is used in the solution for the orientation of the individual links in segment j. The minimized cost function can minimize angle, change in angle, deviation from equal angle, some combination of the three, or another cost function.

This kinematic fitting process is used for each segment in endoscope 400 for which global position data is available. The solution provides in a memory a configuration for endoscope 400 including a global position for each joint.

Figure 6A:
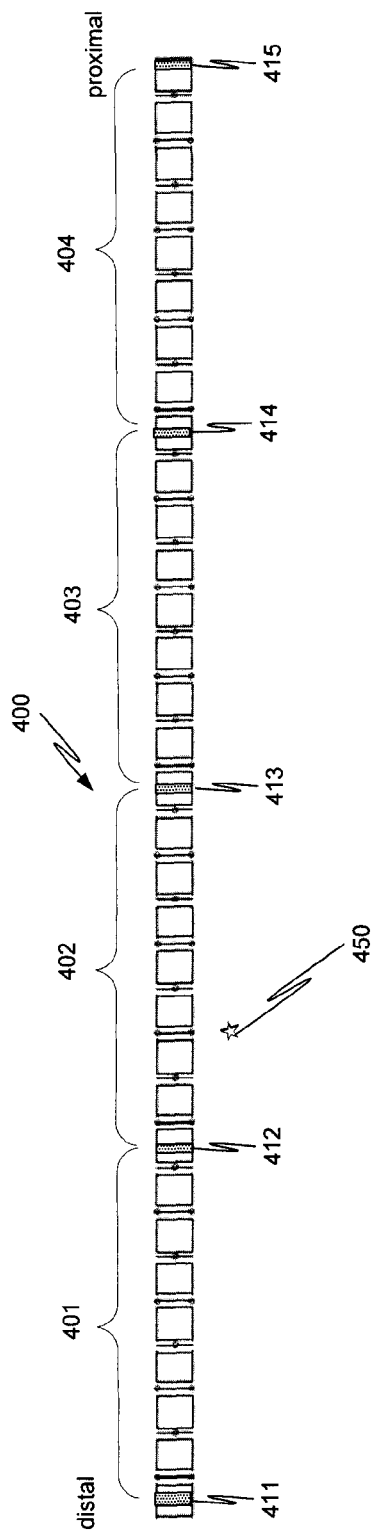
FIG. 6A is a diagrammatic view of the steerable endoscope of FIG. 4A with the foundation point located in the second segment.
Figure 6B:
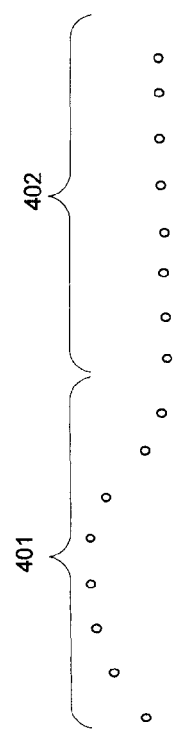
FIG. 6B is a diagrammatic view of locations generated for the steerable endoscope of FIG. 6A.
Figure 6C:
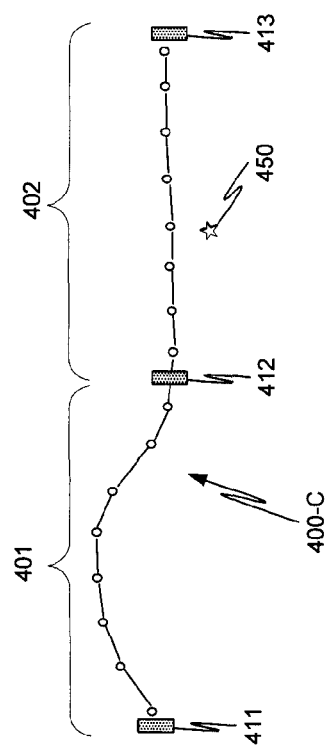
FIG. 6C is a diagrammatic view of a centerline representation for the steerable endoscope of FIG. 6A.

For example, in FIG. 6A, foundation point 450 is bounded by global position sensors 412 and 413 and so is located in second segment 402. Use of the kinematic model provides data points such as those illustrated in FIG. 6B for segments 401, 402. In one aspect, a straight line fit is done between the points of segments 401, 402 to obtain a centerline representation 400-C of steerable endoscope 400.

A length L of centerline 400-C distal to foundation point 450 is the length of endoscope 400 that is inserted. Length L is compared to segment lengths to determine the number of segments active and articulating. Centerline 400-C is used in determining distances to foundation point 450 from various global sensor positions.

Figure 5:
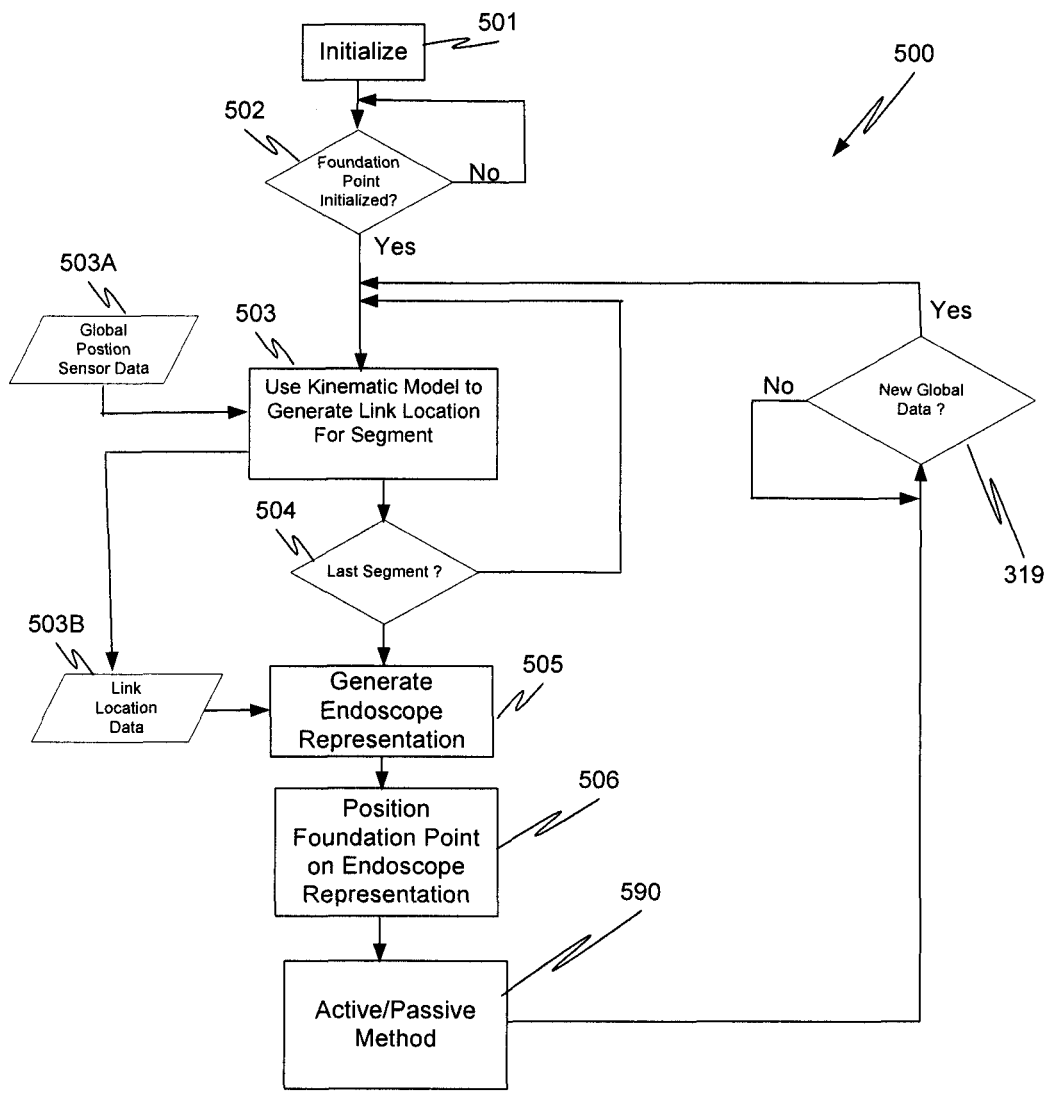
FIG. 5 is a process flow diagram for one method of determining a number of active segments and a number of articulating segments using a kinematic model of a steerable endoscope.

Method 500 in FIG. 5 is one example of using a kinematic model in determining the number of active and articulating segments inserted in a patient. Again, in method 500, a segment is active if any part of the segment has passed foundation point 450. The segment is active and articulating if half or more of the segment has passed foundation point 450. However, with method 500, various points in a segment could be used to make a segment articulating, because by walking centerline 400-C the positions can be determined more accurately than in method 300.

Use of the half-way point to change the state of a segment from active to active and articulating is illustrative only and is not intended to be limiting. In view of this disclosure, one knowledgeable in the field can select criteria relative to the foundation point for sending segments active and articulating based on the particular steerable medical device and procedure of interest. Irrespective of the criteria, the position of foundation point 450 is known.

Initially, in method 500, INITIALIZE operation 501 initializes elements used in method 500. For example, a number of segments active variable NumAct is set to one; a number of segments articulating variable NumArt is set to one; and a maximum count variable countMax is set to five.

Upon completion of INITIALIZE operation 501, method 500 remains in FOUNDATION POINT INITIALIZED check operation 502, until foundation point 450 is initialized. When the tip of endoscope 400 reaches the point that the operator wants to use as a foundation point, the operator takes an action that initializes foundation point 450 as the current location of the tip. The particular action taken by the operator is not essential so long as the system recognizes the action, e.g., pushing a button, and uses the current position of the endoscope tip as foundation point 450.

Also, check operation 502 should not be interpreted as requiring polling. Check operation 502, for example, could be implemented as part of an event handler and when a foundation point initialized event occurs, processing transfers to USE KINEMATIC MODEL TO GENERATE LINK LOCATIONS FOR SEGMENT process 503.

USE KINEMATIC MODEL TO GENERATE LINK LOCATIONS FOR SEGMENT process 503, in one aspect, uses the kinematic model described above with respect to FIG. 4B to generate the locations for links in a segment. Specifically, global position data for the appropriate global position sensors is retrieved from global position sensor data 503A. The kinematic model is processed with the constrained minimization and a minimized cost function, as described above, to obtain link location data that is stored in link location data 503B. Upon completion of processing the segment, process 503 transfers to LAST SEGMENT CHECK operation 504.

LAST SEGMENT CHECK operation 504 determines whether all the segments have been processed by the kinematic model. In one aspect, a quality number is provided for each sensor bounding a segment. If additional segments bounded by sensors having valid quality numbers exist, not all segments have been processed. If the necessary segments have been processed, check operation 504 transfers to GENERATE ENDOSCOPE REPRESENTATION operation 505 and otherwise returns to process 503.

GENERATE ENDOSCOPE REPRESENTATION operation 505 retrieves the data from link location data 503B and generates a centerline representation of endoscope 400. Upon completion, GENERATE ENDOSCOPE REPRESENTATION operation 505 transfers processing to POSITION FOUNDATION POINT ON ENDOSCOPE REPRESENTATION operation 506.

POSITION FOUNDATION POINT ON ENDOSCOPE REPRESENTATION operation 506 finds the point in the centerline representation of endoscope 400 that is closest to the location of foundation point 450. This point is used to determine the insertion depth of endoscope 400, which is the distance along the centerline representation distal to this point.

In some embodiments, POSITION FOUNDATION POINT ON ENDOSCOPE REPRESENTATION operation 506 increments or decrements the insertion depth to compensate for global position sensor errors or movement of foundation point 450 relative to the global reference frame. In one aspect, an offset is added to the determined insertion depth before comparison to segments lengths is done.

In one aspect, upon completion, operation 506 transfers processing to ACTIVE/PASSIVE method 590. in ACTIVE/PASSVIE method 590, the lengths of each segment starting with distal segment 401 are added together and compared with the insertion depth, e.g., the length of segment 401 is compared with the insertion depth; the length of segments 401 and 402 is compared with insertion depth, etc.

Based on the insertion depth, the number of complete segments and any partial segment that have been inserted past the foundation point is determined. Each segment that is completely inserted has state active and state articulating. For a segment that is partially inserted, the state is active and the percentage of the segment inserted is used to determine whether the state articulating is appropriate.

Thus, all segments that are active and do not contain the foundation point are articulating. If the foundation point is more than a specified distance from the distal end of the most proximal active segment, the most proximal active segment is also articulating. In making these determinations, low passing filtering and hysteresis is included in one aspect.

Upon sending the number of active segments and the number of articulating segments in a command to the motors of endoscope 400, method 590 transfers processing to NEW GLOBAL DATA check operation 319 that was described above and that description is incorporated herein by reference. Hence, in one aspect, method 500 is repeated each time a new set of global position data is received.

FIG. 7 is a diagrammatic illustration of an apparatus 775 that can implement any of the above described techniques to determine insertion depth of a steerable endoscope and consequently, the number of active segments and the number of articulating segments. A steerable endoscope 700, or other steerable medical device, is coupled to a medical device controller 740 in system controller 720. A steering controller 745 is also connected to medical device controller 740. Steering controller 745, in one aspect includes a mechanism for an operator to initialize the foundation point, e.g. a button to push or simply pushing down on a joystick for a predetermined period of time. In one aspect, medical device controller 740 includes the motors referenced above.

A sensing system that senses the positions of the position sensors on steerable endoscope 700 is connected to a position controller 725 in system controller 720. A display controller 735 in system controller 720 receives video data from steerable endoscope 700 and displays that data on display device 710. A memory 730, in one aspect, has stored therein, position data 731; a method 300 module 732; and a method 500 module 733. The method modules 732, 733 include at least some of the instructions executed by a processor in processor module 750 in performing methods 300 and 500 or any equivalent method. Also, in one aspect, memory 730 has stored therein data and any other information needed in the execution of the methods.

System controller 720 is illustrated as a unified structure in FIG. 7 for ease of illustration and understanding. This is illustrative only and is not intended to be limiting. The various component of system controller 720 can be located apart and still perform the functions described.

In the Figs., two-dimensional representations have been used for convenience. The drawings should not be interpreted as limiting the description to only a two-dimensional coordinate system, because the various aspects are carried out in a three-dimensional coordinate system. As is known to one knowledgeable in the field, the global position data for a global position sensor includes at least x-coordinate, y-coordinate, and z-coordinate values and so the various distances etc. discussed above are determined in a three-dimensional coordinate system. Further, in view of the description, one knowledgeable in the field can determine each of the defined distances in such a three-dimensional coordinate system.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

The term "flexible" in association with a mechanical structure or component should be broadly construed. In essence, it means the structure or component can be bent without harm. For example, a flexible mechanical structure may include a series of closely spaced components that are similar to "vertebrae" in a snake-like arrangement. In such an arrangement, each component is a short link in a kinematic chain, and movable mechanical constraints (e.g., pin hinge, cup and ball, and the like) between each link may allow one (e.g., pitch) or two (e.g., pitch and yaw) degrees of freedom (DOF) of relative movement between the links. As another example, a flexible mechanical structure may be continuous, such as a closed bendable tube (e.g., nitinol, polymer, and the like) or other bendable piece (e.g., kerf-cut tube, helical coil, and the like). Accordingly, a short, flexible structure may serve as, and be modeled as, a single mechanical constraint (joint) providing one or more DOFs between two links in a kinematic chain, even though the structure itself may be a kinematic chain made of several coupled links.

While the memory in FIG. 7 is illustrated as a unified structure, this should not be interpreted as requiring that all memory is at the same physical location. All or part of the memory can be in a different physical location than a processor. Memory refers to a volatile memory, a non-volatile memory, or any combination of the two.

A processor is coupled to a memory containing instructions executed by the processor. This could be accomplished within a computer system, or alternatively via a connection to another computer via modems and analog lines, or digital interfaces and a digital carrier line.

Herein, a computer program product comprises a medium configured to store computer readable code needed for any one or any combination of the operations described with respect to modules 732, 733 or in which computer readable code for any one or any combination of operations described with respect to module 732, 733 is stored. Some examples of computer program products are CD-ROM discs, DVD discs, flash memory, ROM cards, floppy discs, magnetic tapes, computer hard drives, servers on a network and signals transmitted over a network representing computer readable program code. A tangible computer program product comprises a tangible medium configured to store computer readable instructions for any one of, or any combination of operations described with respect to modules 732, 733 or in which computer readable instructions for any one of, or any combination of operations described with respect to the shape information processing module are stored. Tangible computer program products are CD-ROM discs, DVD discs, flash memory, ROM cards, floppy discs, magnetic tapes, computer hard drives and other physical storage mediums.

In view of this disclosure, instructions used in any one of, or any combination of operations described with respect to modules 732, 733 can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

I claim:

1. A method comprising:
   receiving, by a processor, a first set of position data for a plurality of position sensors on a steerable medical device,
     wherein said steerable medical device includes a plurality of articulatable segments;
     wherein each articulatable segment of the plurality of articulatable segments includes a serial combination of three or more links, and wherein each link in the three or more links is coupled to another link in the three or more links by a joint;
     wherein a first position sensor of said plurality of position sensors is mounted on a distal end of a distal articulatable segment of said plurality of articulatable segments;
     wherein a second position sensor of said plurality of position sensors is mounted on a proximal end of a proximal articulatable segment of said plurality of articulatable segments; and
     wherein a different position sensor of said plurality of position sensors is mounted between each of said plurality of articulatable segments so that the each articulatable segment of said plurality of articulatable segments is bounded by a different pair of position sensors of said plurality of position sensors;
   determining, by said processor using said first set of position data and a foundation point, a number of said plurality of articulatable segments having an active state and a number of said plurality of articulatable segments having an active state and an articulating state,
     wherein an articulating segment of said plurality of articulatable segments is counted by the processor as having an active state if the articulating segment is completely or partially inserted into a patient past the foundation point,
     wherein an articulating segment of said plurality of articulatable segments is counted by the processor as having an active state and an articulating state if more than a predetermined percentage of the articulating segment is inserted into the patient past the foundation point; and
   sending, by said processor to a controller for said steerable medical device, a command to configure said steerable medical device to have said number of said plurality of articulatable segments having said active state and said number of said plurality of articulatable segments having said active state and said articulating state.

2. The method of claim 1, wherein said determining further comprises:
  analyzing (1) data of a proximal position sensor of the pair of position sensors bounding an articulatable segment of said plurality of articulatable segments in said first set of position data to determine a position of said proximal position sensor relative to said foundation point, and (2) data of a distal position sensor of the pair of position sensors bounding an articulatable segment of said plurality of articulatable segments in said first set of position data to determine a position of said distal position sensor relative to said foundation point.

3. The method of claim 2, wherein said proximal position sensor and distal position sensor bound a most proximal segment having an active state.

4. The method of claim 2, wherein said analyzing further comprises:
  determining a distance $d_{fi}$ from said proximal position sensor to said foundation point;
  determining a distance $d_{f(i-1)}$ from said distal position sensor to said foundation point; and
  determining a distance $d_{i(i-1)}$ from said proximal position sensor to said distal position sensor.

5. The method of claim 4, wherein said analyzing further comprises:
  comparing said distance $d_{fi}$ and said distance $d_{f(i-1)}$ to determine whether distance $d_{fi}$ is less than distance $d_{f(i-1)}$.

6. The method of claim 5, wherein said analyzing further comprises:
  changing said number of said plurality of articulatable segments having said active state and said articulating state following said comparing finding said distance $d_{fi}$ is less than distance $d_{f(i-1)}$.

7. The method of claim 4, wherein said analyzing further comprises:
  comparing said distance $d_{f(i-1)}$ and said distance $d_{i(i-1)}$ to determine whether distance $d_{f(i-1)}$ is greater than distance $d_{i(i-1)}$.

8. The method of claim 7, wherein said analyzing further comprises:
  changing said number of said plurality of articulatable segments having said active state following said comparing finding said distance $d_{f(i-1)}$ is greater said than distance $d_{i(i-1)}$.

9. The method of claim 1, further comprising:
  initializing said foundation point prior to said determining.

10. The method of claim 1, wherein said determining said number of said plurality of articulatable segments having an active state and said number of said plurality of articulatable segments having an active state and an articulating state further comprises:
  determining locations of the three or more links in at least one articulatable segment of the plurality of articulatable segments using a kinematic model for said at least one articulatable segment.

11. The method of claim 10, further comprising:
  performing said determining locations for each articulatable segment in said plurality of articulatable segments.

12. The method of claim 10, wherein said determining locations further comprises:
  determining an orientation of each of said links of the three or more links.

13. The method of claim 10, wherein said determining said number of said plurality of articulatable segments having said active state and said number of said plurality of articulatable segments having said active state and the articulating state further comprises:
  generating a centerline representation of said steerable medical device using said locations.

14. The method of claim 13, wherein said determining said number of said plurality of articulatable segments having said active state and said number of said plurality of articulatable segments having said active state and the articulating state further comprises:
  determining an insertion depth of said steerable medical device using said centerline representation.

15. An apparatus comprising:
  a steerable medical device comprising a plurality of articulatable segments and a plurality of position sensors,
    each articulatable segment of the plurality of articulatable segments including a serial combination of three or more links, each link in the three or more links being coupled to another link in the three or more links by a joint,
    a first position sensor of said plurality of position sensors being mounted on a distal end of a distal articulatable segment of said plurality of articulatable segments,
    a second position sensor of said plurality of position sensors being mounted on a proximal end of a proximal articulatable segment of said plurality of articulatable segments, and
  a different position sensor of said plurality of position sensors being mounted between each of said plurality of articulatable segments so that the each articulatable segment of said plurality of articulatable segments is bounded by a different pair of position sensors of said plurality of position sensors;
  a controller, coupled to said steerable medical device, comprising:
    a processor, coupled to said steerable medical device, configured to receive position data for said plurality of sensors, and configured to receive data defining a foundation point; and
    a steerable medical device controller coupled to said steerable medical device,
      wherein the steerable medical device controller is configured to configure said plurality of articulatable segments,
      wherein said processor is configured to analyze said position data with reference to said foundation point to determine a number of said plurality of articulatable segments having an active state and a number of said plurality of articulatable segments having an active state and an articulating state,
      wherein an articulating segment of said plurality of articulatable segments is counted by the processor as having an active state if the articulating segment is completely or partially inserted into a patient past the foundation point,
      wherein an articulating segment of said plurality of articulatable segments is counted by the processor as having an active state and an articulating state if more than a predetermined percentage of the articulating segment is inserted into the patient past the foundation point, and
      wherein said processor is configured to output a command to said steerable medical device controller to configure said steerable medical device to have said number of said plurality of articulatable segments having said active state and to have said number of said plurality of articulatable segments having said active state and said articulating state.

16. The apparatus of claim 15, wherein said processor is configured to analyze said position data with reference to said foundation point further comprises:
- said processor being configured to determine from said received position data a distance $d_{fi}$ from said foundation point to a proximal position sensor of the pair of position sensors bounding an articulatable segment of said plurality of articulatable segments;
- said processor being configured to determine, from said received position data, a distance $d_{f(i-1)}$ from said foundation point to a distal position sensor of the pair position sensors bounding an articulatable segment of said plurality of articulatable segments; and
- said processor being configured to determine a distance $d_{i(i-1)}$ from said proximal position sensor to said distal position sensor.

17. The apparatus of claim 16, wherein said processor is configured to analyze said position data with reference to said foundation point further comprises:
- said processor configured to compare said distance $d_{fi}$ and said distance $d_{f(i-1)}$ to determine whether distance $d_{fi}$ is less than distance $d_{f(i-1)}$; and
- said processor configured to change said number of said plurality of articulatable segments having said active state and said articulating state following said comparing finding said distance $d_{fi}$ is less than distance $d_{f(i-1)}$.

18. The apparatus of claim 16, wherein said processor is configured to analyze said position data with reference to said foundation point further comprises:
- said processor configured to compare said distance $d_{f(i-1)}$ and said distance $d_{i(i-1)}$ to determine whether distance $d_{f(i-1)}$ is greater than distance $d_{i(i-1)}$; and
- said processor configured to change said number of said plurality of articulatable segments having said active state following said comparing finding said distance $d_{f(i-1)}$ is greater than distance $d_{i(i-1)}$.

19. The apparatus of claim 15, wherein said processor is configured to analyze said position data with reference to said foundation point further comprises:
- said processor being configured to determine locations of the three or more links in one articulatable segment of the plurality of articulatable segments using a kinematic model for said one articulatable segment.

20. The apparatus of claim 19, wherein said processor is configured to analyze said position data with reference to said foundation point further comprises:
- said processor being configured to generate a centerline representation of said medical device using said locations.

* * * * *